United States Patent
Markovic

(10) Patent No.: US 11,571,469 B2
(45) Date of Patent: Feb. 7, 2023

(54) METHODS OF TREATING CANCER WITH INTERFERON WHEREIN THE CANCER CELLS ARE HLA NEGATIVE OR HAVE REDUCED HLA EXPRESSION

(71) Applicant: Mayo Foundation for Medical Education and Research, Rochester, MN (US)

(72) Inventor: Svetomir N. Markovic, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 412 days.

(21) Appl. No.: 16/068,392

(22) PCT Filed: Jan. 6, 2017

(86) PCT No.: PCT/US2017/012580
§ 371 (c)(1),
(2) Date: Jul. 6, 2018

(87) PCT Pub. No.: WO2017/120501
PCT Pub. Date: Jul. 13, 2017

(65) Prior Publication Data
US 2019/0022188 A1    Jan. 24, 2019

Related U.S. Application Data

(60) Provisional application No. 62/276,198, filed on Jan. 7, 2016.

(51) Int. Cl.
| | |
|---|---|
| *A61K 35/17* | (2015.01) |
| *A61K 38/21* | (2006.01) |
| *A61P 35/00* | (2006.01) |
| *A61K 39/395* | (2006.01) |
| *A61K 45/06* | (2006.01) |
| *A61K 39/00* | (2006.01) |

(52) U.S. Cl.
CPC .......... *A61K 39/0011* (2013.01); *A61K 35/17* (2013.01); *A61K 38/212* (2013.01); *A61K 39/00* (2013.01); *A61K 39/39558* (2013.01); *A61K 45/06* (2013.01); *A61P 35/00* (2018.01); *A61K 2039/5158* (2013.01); *A61K 2039/55522* (2013.01)

(58) Field of Classification Search
None
See application file for complete search history.

(56) References Cited

U.S. PATENT DOCUMENTS

| | | |
|---|---|---|
| 4,350,687 A | 9/1982 | Lipton et al. |
| 5,026,772 A | 6/1991 | Kobayashi et al. |
| 5,116,944 A | 5/1992 | Sivam et al. |
| 5,216,130 A | 6/1993 | Line et al. |
| 5,252,713 A | 10/1993 | Morgan, Jr. et al. |
| 5,260,308 A | 11/1993 | Poduslo et al. |
| 5,728,541 A | 3/1998 | Kornblith |
| 5,736,137 A | 4/1998 | Anderson et al. |
| 6,054,297 A | 4/2000 | Carter et al. |
| 6,147,060 A | 11/2000 | Zasloff et al. |
| 6,416,967 B2 | 7/2002 | Kornblith |
| 6,537,579 B1 | 3/2003 | Desai et al. |
| 6,933,129 B1 | 8/2005 | Kornblith |
| 7,041,301 B1 | 5/2006 | Markovic |
| 7,112,409 B2 | 9/2006 | Blumenthal et al. |
| 7,678,552 B2 | 3/2010 | Kornblith |
| 7,731,950 B2 | 6/2010 | Noessner et al. |
| 7,758,891 B2 | 7/2010 | Desai et al. |
| 7,820,788 B2 | 10/2010 | Desai et al. |
| 7,906,121 B2 | 3/2011 | Chang et al. |
| 7,923,536 B2 | 4/2011 | Desai et al. |
| 8,034,375 B2 | 10/2011 | Desai et al. |
| 8,119,129 B2 | 2/2012 | Jure-Kunkel et al. |
| 8,138,229 B2 | 3/2012 | Desai et al. |
| 8,268,348 B2 | 9/2012 | Desai et al. |
| 8,314,156 B2 | 11/2012 | Desai et al. |
| 8,344,177 B2 | 1/2013 | Neri et al. |
| 8,735,394 B2 | 5/2014 | Desai et al. |
| 8,853,260 B2 | 10/2014 | Desai et al. |
| 9,101,543 B2 | 8/2015 | Desai et al. |
| 9,387,244 B2 | 7/2016 | Markovic |
| 9,427,477 B2 | 8/2016 | Markovic et al. |
| 9,446,148 B2 | 9/2016 | Markovic et al. |
| 9,533,058 B2 | 1/2017 | Markovic et al. |

(Continued)

FOREIGN PATENT DOCUMENTS

| | | |
|---|---|---|
| EP | 1913947 | 4/2008 |
| EP | 3204413 | 8/2017 |

(Continued)

OTHER PUBLICATIONS

IntronA, Cneter watch pp. 1-7, (Year: 1995).*
Ulvestad et al., (1994), Immunology, vol. 82, pp. 535-541 (Year: 1994).*
U.S. Appl. No. 15/225,542, office action dated Jan. 14, 2020.
U.S. Appl. No. 15/225,542; office action dated Jul. 30, 2020.
U.S. Appl. No. 15/286,024, office action dated Feb. 10, 2020.
U.S. Appl. No. 15/286,024, office action dated Jul. 29, 2020.
U.S. Appl. No. 15/359,569; office action dated Jan. 17, 2020.
U.S. Appl. No. 15/430,411, office action dated Apr. 17, 2020.
U.S. Appl. No. 15/452,669; office action dated Mar. 3, 2020.
U.S. Appl. No. 15/456,377; office action dated Mar. 12, 2020.

(Continued)

*Primary Examiner* — Robert S Landsman
(74) *Attorney, Agent, or Firm* — Baker Botts L.L.P.

(57) ABSTRACT

The invention described herein relates to methods for treating a patient having a plurality of HLA-negative cancer cells or cancer cells with reduced HLA expression with IFN-alpha in an amount sufficient to expand and/or activate immune cells such that the activated and/or expanded immune cells kill one or more of HLA-negative cancer cells or the cancer cells with reduced HLA expression.

8 Claims, No Drawings

(56) References Cited

U.S. PATENT DOCUMENTS

| | | |
|---|---|---|
| 9,555,128 B2 | 1/2017 | Markovic et al. |
| 9,566,350 B2 | 2/2017 | Markovic et al. |
| 9,757,453 B2 | 9/2017 | Markovic et al. |
| 10,279,035 B2 | 5/2019 | Markovic et al. |
| 10,279,036 B2 | 5/2019 | Markovic et al. |
| 10,300,016 B2 | 5/2019 | Markovic et al. |
| 10,307,482 B2 | 6/2019 | Markovic et al. |
| 10,322,084 B2 | 6/2019 | Markovic et al. |
| 10,376,579 B2 | 8/2019 | Markovic et al. |
| 10,376,580 B2 | 8/2019 | Markovic et al. |
| 10,391,055 B2 | 8/2019 | Markovic et al. |
| 10,406,224 B2 | 9/2019 | Markovic et al. |
| 10,413,606 B2 | 9/2019 | Markovic et al. |
| 10,420,839 B2 | 9/2019 | Markovic et al. |
| 10,441,656 B2 | 10/2019 | Markovic et al. |
| 10,471,145 B2 | 11/2019 | Markovic et al. |
| 10,478,495 B2 | 11/2019 | Markovic et al. |
| 10,493,150 B2 | 12/2019 | Markovic et al. |
| 10,507,243 B2 | 12/2019 | Markovic et al. |
| 10,561,726 B2 | 2/2020 | Swiss et al. |
| 10,596,111 B2 | 3/2020 | Markovic et al. |
| 10,596,112 B2 | 3/2020 | Markovic et al. |
| 10,610,484 B2 | 4/2020 | Markovic et al. |
| 10,618,969 B2 | 4/2020 | Markovic et al. |
| 10,624,846 B2 | 4/2020 | Markovic et al. |
| 10,668,151 B2 | 6/2020 | Markovic et al. |
| 10,765,741 B2 | 9/2020 | Markovic et al. |
| 10,772,833 B2 | 9/2020 | Markovic et al. |
| 10,780,049 B2 | 9/2020 | Markovic et al. |
| 10,780,050 B2 | 9/2020 | Markovic et al. |
| 2002/0111362 A1 | 8/2002 | Rubinfeld |
| 2004/0005318 A1 | 1/2004 | Davis et al. |
| 2004/0077601 A1 | 4/2004 | Adams et al. |
| 2005/0032699 A1 | 2/2005 | Holash et al. |
| 2006/0165652 A1 | 7/2006 | Dudley et al. |
| 2007/0020232 A1 | 1/2007 | Rossignol et al. |
| 2007/0148135 A1 | 6/2007 | Dang et al. |
| 2007/0166388 A1 | 7/2007 | Desai et al. |
| 2009/0004118 A1 | 1/2009 | Nie et al. |
| 2010/0047234 A1 | 2/2010 | Markovic |
| 2010/0092489 A1 | 4/2010 | Van De Winkel et al. |
| 2010/0112077 A1 | 5/2010 | Desai et al. |
| 2010/0172835 A1 | 7/2010 | Ruoslahti et al. |
| 2010/0260679 A1 | 10/2010 | Shachar et al. |
| 2010/0311679 A1 | 12/2010 | Olson et al. |
| 2011/0014117 A1 | 1/2011 | Wang et al. |
| 2011/0076273 A1 | 3/2011 | Adler et al. |
| 2011/0097340 A1 | 4/2011 | Ramachandra et al. |
| 2011/0104143 A1 | 6/2011 | Buchsbaum et al. |
| 2011/0150902 A1 | 6/2011 | Markovic |
| 2011/0262525 A1 | 10/2011 | Wang et al. |
| 2012/0263739 A1 | 10/2012 | Langer et al. |
| 2012/0315273 A1 | 12/2012 | Markovic |
| 2013/0028895 A1 | 1/2013 | Wulf |
| 2013/0071403 A1 | 3/2013 | Rolland et al. |
| 2013/0149238 A1 | 6/2013 | Kavlie et al. |
| 2013/0164816 A1 | 6/2013 | Chang et al. |
| 2014/0056909 A1 | 2/2014 | Markovic |
| 2014/0155344 A1 | 6/2014 | Neil et al. |
| 2014/0161819 A1 | 6/2014 | Hann et al. |
| 2014/0178486 A1 | 6/2014 | Markovic et al. |
| 2014/0302017 A1 | 10/2014 | Markovic |
| 2014/0314774 A1 | 10/2014 | Zhou et al. |
| 2015/0050356 A1 | 2/2015 | Desai et al. |
| 2015/0246122 A1 | 9/2015 | Markovic et al. |
| 2016/0095942 A1 | 4/2016 | Markovic et al. |
| 2016/0184229 A1 | 6/2016 | Markovic et al. |
| 2016/0184452 A1 | 6/2016 | Markovic et al. |
| 2016/0184453 A1 | 6/2016 | Markovic et al. |
| 2016/0235860 A1 | 8/2016 | Markovic et al. |
| 2016/0250351 A1 | 9/2016 | Markovic et al. |
| 2016/0256431 A1 | 9/2016 | Markovic et al. |
| 2016/0263241 A1 | 9/2016 | Markovic et al. |
| 2016/0310610 A1 | 10/2016 | Markovic et al. |
| 2016/0324964 A1 | 11/2016 | Markovic et al. |
| 2016/0338961 A1 | 11/2016 | Markovic et al. |
| 2016/0339118 A1 | 11/2016 | Markovic et al. |
| 2017/0021023 A1 | 1/2017 | Dikstein |
| 2017/0021032 A1 | 1/2017 | Markovic et al. |
| 2017/0021034 A1 | 1/2017 | Markovic et al. |
| 2017/0071897 A1 | 3/2017 | Markovic et al. |
| 2017/0095574 A1 | 4/2017 | Swiss et al. |
| 2017/0100492 A1 | 4/2017 | Markovic et al. |
| 2017/0106087 A1 | 4/2017 | Markovic et al. |
| 2017/0128408 A1 | 5/2017 | Markovic et al. |
| 2017/0128583 A1 | 5/2017 | Markovic et al. |
| 2017/0128584 A1 | 5/2017 | Markovic et al. |
| 2017/0128585 A1 | 5/2017 | Markovic et al. |
| 2017/0128586 A1 | 5/2017 | Markovic et al. |
| 2017/0128587 A1 | 5/2017 | Markovic et al. |
| 2017/0128588 A1 | 5/2017 | Markovic et al. |
| 2017/0182174 A1 | 6/2017 | Markovic et al. |
| 2017/0182175 A1 | 6/2017 | Markovic et al. |
| 2017/0182180 A1 | 6/2017 | Markovic et al. |
| 2017/0182183 A1 | 6/2017 | Markovic et al. |
| 2017/0182184 A1 | 6/2017 | Markovic et al. |
| 2017/0182185 A1 | 6/2017 | Markovic et al. |
| 2017/0182186 A1 | 6/2017 | Markovic et al. |
| 2017/0182187 A1 | 6/2017 | Markovic et al. |
| 2017/0196831 A1 | 7/2017 | Markovic et al. |
| 2017/0196832 A1 | 7/2017 | Markovic et al. |
| 2017/0196833 A1 | 7/2017 | Markovic et al. |
| 2017/0216453 A1 | 8/2017 | Markovic et al. |
| 2017/0232102 A1 | 8/2017 | Markovic et al. |
| 2017/0291952 A1 | 10/2017 | Markovic et al. |
| 2018/0235886 A1 | 8/2018 | Markovic et al. |
| 2019/0038761 A1 | 2/2019 | Markovic et al. |
| 2019/0099498 A1 | 4/2019 | Markovic et al. |
| 2019/0184032 A1 | 6/2019 | Markovic et al. |
| 2019/0201546 A1 | 7/2019 | Markovic et al. |
| 2019/0202916 A1 | 7/2019 | Markovic et al. |
| 2019/0216944 A1 | 7/2019 | Markovic et al. |
| 2020/0237907 A1 | 7/2020 | Swiss et al. |
| 2020/0268884 A1 | 8/2020 | Markovic et al. |
| 2020/0308294 A1 | 10/2020 | Markovic et al. |

FOREIGN PATENT DOCUMENTS

| | | |
|---|---|---|
| EP | 3533870 | 9/2019 |
| JP | S60146833 | 8/1985 |
| JP | S6178731 | 4/1986 |
| JP | H04504253 | 7/1992 |
| JP | 2001072589 | 3/2001 |
| JP | 2012522809 | 9/2012 |
| KR | 1020090078330 | 7/2009 |
| RU | 2011133819 | 2/2013 |
| RU | 2505315 C2 | 1/2014 |
| WO | 89/10398 | 11/1989 |
| WO | 97/49390 | 12/1997 |
| WO | 99/00113 | 1/1999 |
| WO | 99/51248 | 10/1999 |
| WO | 2004/022097 | 3/2004 |
| WO | 2004/096224 | 11/2004 |
| WO | 2006/034455 | 3/2006 |
| WO | 2006/089290 | 8/2006 |
| WO | 2007/027819 | 3/2007 |
| WO | 2007/027941 | 3/2007 |
| WO | 2008/047272 | 4/2008 |
| WO | 2008/057562 | 4/2008 |
| WO | 2008/057561 | 5/2008 |
| WO | 2008076373 A1 | 6/2008 |
| WO | 2008/112987 | 9/2008 |
| WO | 2009/043159 | 4/2009 |
| WO | 2009/055343 | 4/2009 |
| WO | 2010/003057 | 1/2010 |
| WO | 2010/017216 | 2/2010 |
| WO | 2010/118365 | 10/2010 |
| WO | 2010/124009 | 10/2010 |
| WO | 2010/136492 | 12/2010 |
| WO | 2012/048223 | 4/2012 |
| WO | 2012/088388 | 6/2012 |
| WO | 2012/154861 | 11/2012 |
| WO | 2014/009774 | 1/2014 |
| WO | 2014/037422 | 3/2014 |

(56) References Cited

FOREIGN PATENT DOCUMENTS

| | | |
|---|---|---|
| WO | 2014/055415 | 4/2014 |
| WO | 2014/105644 | 7/2014 |
| WO | 2014/123612 | 8/2014 |
| WO | 2015/048520 | 4/2015 |
| WO | 2015/191969 | 12/2015 |
| WO | 2015/195476 | 12/2015 |
| WO | 2016/057554 | 4/2016 |
| WO | 2016/059220 | 4/2016 |
| WO | 2016/089873 | 6/2016 |
| WO | 2017/031368 | 2/2017 |
| WO | 2017/062063 | 4/2017 |
| WO | 2017/120501 | 7/2017 |
| WO | 2017/139698 | 8/2017 |
| WO | 2017/165439 | 9/2017 |
| WO | 2017/165440 | 9/2017 |
| WO | 2017/176265 | 10/2017 |
| WO | 2018/027205 | 2/2018 |
| WO | 2018/045238 | 3/2018 |
| WO | 2018/045239 | 3/2018 |
| WO | 2018/048815 | 3/2018 |
| WO | 2018/048816 | 3/2018 |
| WO | 2018/048958 | 3/2018 |

OTHER PUBLICATIONS

U.S. Appl. No. 15/456,391; office action dated Feb. 4, 2020.
U.S. Appl. No. 15/460,699; office action dated Mar. 3, 2020.
U.S. Appl. No. 15/461,288; office action dated Feb. 28, 2020.
U.S. Appl. No. 15/675,596; office action dated May 28, 2020.
U.S. Appl. No. 15/752,155; office action dated Feb. 7, 2020.
U.S. Appl. No. 16/328,146; office action dated Feb. 26, 2020.
U.S. Appl. No. 16/328,146; office action dated Jul. 28, 2020.
Barua et al. "Particle shape enhances specificity of antibody-display nanoparticles", PNAS 110(9):3270-3275 (2013).
Chuang et al. "Recombinant human serum albumin", Drugs Today 43(8):547-561 (2007) (Abstract Only) (2 pages).
European Application No. 17750912.2 Extended European Search Report dated Jan. 2, 2020.
Miele et al. "Albumin-bound formulation of paclitaxel (Abraxane® ABI-007) in the treatment of breast cancer", International Journal of Nanomedicine 4:99-105 (2009).
Warner et al. "Alemtuzumab use in relapsed and refractory chronic lymphocytic leukemia: a history and discussion of future rational use", Ther Adv Hematol 3(6):375-389 (2012).
Zhao et al. "Abraxane, the Nanopartide Formulation of Paclitaxel Can Induce Drug Resistance by Ip-Regulation of P-gp", PLoS One 10(7):e0131429 (2015) (19 pages).
U.S. Appl. No. 15/359,569; office action dated Aug. 10, 2020.
"U.S. Appl. No. 15/430,411, office action dated Nov. 2, 2020".
"U.S. Appl. No. 15/452,669: office action dated Oct. 21, 2020".
"U.S. Appl. No. 15/456,377; office action dated Sep. 1, 2020".
"U.S. Appl. No. 15/675,596; office action dated Oct. 20, 2020".
"U.S. Appl. No. 16/086,977; office action dated Sep. 3, 2020".
"U.S. Appl. No. 16/330,028; office action dated Nov. 24, 2020".
Stefan Einhorn et al., "Interferon and Natural Killer Activity in Multiple Myeloma. Lack of Correlation Between Interferon-Induced Enhancement of Natural Killer Activity and Clinical Response to Human Interferon-α", Int. J. Cancer 30, 167-172 (1982), Received Apr. 13, 1982.
Bruce S. Edwards et al., "Low Doses of Interferon Alpha Result in More Effective Clinical Natural Killer Cell Activation", J. Clin. Invest., The American Society for Clinical Investigation, Inc., vol. 75, Jun. 1985, 1908-1913, Jun. 1985.
FDA label—Product Information INTRON® A Interferon alfa-2b, recombinant for Injection, by Schering Corporation, a subsidiary of Merck & Co. Inc., Rev. Aug. 2014, 57 pages, Aug. 2014.
Liang et al. "IFN-alpha regulates NK ceil cytotoxicity through STAT1 pathway," Cytokine, Aug. 13, 2003 (Aug. 13, 2013), vol. 23, pp. 190-199.
Makridis, et al., "MHC class I and II antigen expression and interferon ? treatment of human midgut carcinoid tumors," World Journal of Surgery, Aug. 1, 1993 (Aug. 1, 1993), vol. 16, Iss. 4, pp. 481-486.
Ortaldo et al., "Effects of several species of human leukocyte interferon on cytotoxic activity of NK cells and monocytes," International Journal of Cancer, Mar. 15, 1983 (Mar. 15, 1983) vol. 31, No. 3, pp. 285-289.
Notification of Transmittal of the International Search Report and the Written Opinion of the International Searching Authority, or the Declaration corresponding to International Application No. PCT/US2017/012580 dated Mar. 17, 2017.
Notification concerning Transmittal of International Preliminary Report on Patentability corresponding to International Application No. PCT/US2017/012580 dated Jul. 19, 2018.
Anonymous "Paclitaxel Albumin-Stabilized Nanoparticle Formulation and Bevacizumab in Treating Patients With Stage IV Melanoma That Cannot Be Removed by Surgery or Gynecological Cancers", NCT02020707, ClinicalTrials.gov, Dec. 25, 2013 (13 pages)
U.S. Appl. No. 15/187,672, office action dated Sep. 11, 2019.
U.S. Appl. No. 15/225,428, office action dated Jul. 31, 2019.
U.S. Appl. No. 15/225,428, office action dated Dec. 6, 2019.
U.S. Appl. No. 15/286,024, office action dated Aug. 1, 2019.
U.S. Appl. No. 15/359,569, office action dated Jul. 26, 2019.
U.S. Appl. No. 15/430,411; office action dated Oct. 31, 2019.
U.S. Appl. No. 15/456,395; office action dated Aug. 14, 2019.
U.S. Appl. No. 15/456,399; office artion dated Aug. 14, 2019.
U.S. Appl. No. 15/460,552, office action dated Aug. 14, 2019.
U.S. Appl. No. 15/460,699; office action dated Aug. 28, 2019.
U.S. Appl. No. 15/461,288; office action dated Aug. 28, 2019.
U.S. Appl. No. 15/752,155; office action dated Dec. 3, 2019.
U.S. Appl. No. 15/752,155; office action dated Sep. 25, 2019.
Cirstoiu-Hapca et al. "Benefit of anti-HER2-coated paclitaxel-loaded immuno-nanpoarticles in the treatment of disseminated ovarian cancer: Therapeutic efficacy and biodistribution in mice", Journal of Controlled Release 144:324-331 (2010).
European Application No. 17771005.0, Extended European Search Report dated Oct. 17, 2019.
European Application No. 17771006.8, Extended European Search Report dated Oct. 16, 2019.
International Preliminary Report on Patentability for Application No. PCT/US2017/050134 dated Mar. 21, 2019.
Liu et al. "Freeze-Drying of Proteins", In: Walkers W., Oldenhof H. (eds) Cryopreservation and Freeze-Drying Protocols. Methods in Molecular Biology (Methods and Protocols), vol. 1257. Springer, New York, NY: published online Nov. 14, 2014.
Reynolds et al. "Phase II Trial of Nanoparticie Albumin-Bound Paditaxel, Carboplatin, and Bevacizumab in First-Line Patients with Advanced Nonsquamous Non-small Cell Lung Cancer", J Thoracic Oncology 4(12):1537-1543 (2009).
"Concurrent Infusions", J Oncol Pract., 4(4): 171, Jul. 2008.
Abraxane® for Injectable Suspension (paclitaxel prolein-bound particles for injectable suspension) (albumin-bound), [drug label], 22 pages, Sep. 2009.
Abraxis Bioscience, Inc., "Abraxane: For the adjuvant treatment of node-positive breast cancer administered sequentially to standard doxorubidn-containing combination chemotherapy," Oncologic Drugs Advisory Committee Meeting (available to public Aug. 4, 2006).
Adams et al., "(P2-11-01) Safety and clinical activity of atezolizumab (anti-PDL1) in combination with nab-paclitaxel in patients with metastatic triple-negative breast cancer", 2015, XP002775314, 2015 San Antonio Breast Cancer Symposium, URL: http://sabcs.org/portals/sabcs2016/documents/sabcs-2015-abstracts.pdf?v=5.
Adams et al., "Phase lb trial of atezolizumab in combination with nab-paditaxel in patients with metastatic triplenegative breast cancer (mTNBC)" Journal of Clinical Oncology col. 34, No. 15, May 1, 2016, 4 pages.
Agarwal et al., "Flow Cytometric analysis of Th1 and Th2 cytokines in PBMCs as a parameter of immunological dysfunction in patients of Superficial Transitional cell carcinoma of bladder", Cancer Immunol. Immunother., 2006, 55(6):734-743.

(56) References Cited

OTHER PUBLICATIONS

Agarwala et al., "Randomized phase III study of paclitaxel plus carboplatin with or without sorafenib as second-line treatment in patients with advanced melanoma", J. Clin. Oncol., 2007, 25(18S):8510 (Abstract).
Allen "Ligand-targeted therapeutics in anticancer therapy, Cancer", Oct. 2002, 2(10), pp. 750-763.
Alley et al. "Contribution of Linker Stability to the Activities of Anticancer Immunoconjugates", Bioconjugate Chem., 2008, 19(3), pp. 759-765.
Anonymous, "A Phase II, muiticenter, randomized, double-blind placebo-controlled trial evaluating the efficacy and safety of bevacizumab in combination with carboplatin and paditaxel chemotherapy for the first-line treatment of patients with metastatic melanoma". U.S. National Institutes of Health, 2007, 3 pages.
Anonymous, "A Phase III, Multicenter, Randomized Placebo-Controlled Study of Atezolizumab (Anti-PD-L1 Antibody) in Combination with Nab Paclitaxel Compared with Placebo with Nab Paclitaxel for Patients with Previously Untreated Metastatic Triple Negative Breast Cancer", ClinicalTrials.gov, Apr. 21, 2015, 1 page
Anonymous, "Atezolizumab Plus Abraxane Promising New Treatment for Tripie-Negative Breast Cancer", UNM Comprehensive Cancer Center, Jan. 7, 2016, pp. 1-2.
Anonymous, "Phase II trial of carboplatin, weekly paclitaxel and biweekly bevacizumab in patients with unresectabl stage IV melanoma", U.S. National Institutes of Health, 2007, 4 pages.
Anonymous, "A Study of Bevacizumab With Carboplatin and Paclitaxel Chemotherapy for the First-Line Treatment of Patients With Metastatic Melanoma (BEAM)," ClinicalTrials.gov [online]. Retrieved from the Internet: URL: https://clinicaitrials.gov/archive/NCT00434252/200703 12, dated Mar. 12, 2007, 3 pages.
U.S. Appl. No. 14/116,619, office action dated Feb. 4, 2015
U.S. Appl. No. 14/116,619, office action dated Apr. 28, 2016.
U.S. Appl. No. 14/116,619, office action dated Sep. 10, 2015.
U.S. Appl. No. 14/432,979, office action dated May 16, 2018.
U.S. Appl. No. 14/432,979, office action dated Jun. 30, 2016.
U.S. Appl. No. 14/432,979, office action dated Oct. 4, 2017.
U.S. Appl. No. 14/432,979, office action dated Dec. 15, 2016
U.S. Appl. No. 14/882,327, office action dated May 2, 2016.
U.S. Appl. No. 15/030,567. office action dated Sep. 7, 2016.
U.S. Appl. No. 15/030,568, office action dated May 25, 2017.
U.S. Appl. No. 15/030,568, office action dated Jun. 18, 2018.
U.S. Appl. No. 15/052,335, office action dated Dec. 1, 2017.
U.S. Appl. No. 15/052,335, office action dated Feb. 9, 2018.
U.S. Appl. No. 15/052,336, office action dated Sep. 4, 2018.
U.S. Appl. No. 15/052,623, office action dated Feb. 9, 2018.
U.S. Appl. No. 15/052,623, office action dated May 19, 2017.
U.S. Appl. No. 15/052,623, office action dated Jul. 9, 2018.
U.S. Appl. No. 15/052,623, office action dated Nov. 25, 2016
U.S. Appl. No. 15/060,967, office action dated Aug. 2, 2016.
U.S. Appl. No. 15/064,396, office action dated Aug. 9, 2016.
U.S. Appl. No. 15/092,403, office action dated Apr. 2, 2018.
U.S. Appl. No. 15/092,403, office action dated Oct. 4, 2018.
U.S. Appl. No. 15/092,433, office action dated Mar. 21, 2018.
U.S. Appl. No. 15/092,433, office action dated Aug. 10, 2018.
U.S. Appl. No. 15/092,433, office action dated Oct. 11, 2017.
U.S. Appl. No. 15/187,672, office action dated May 31, 2018.
U.S. Appl. No. 15/202,115, office action dated Jan. 20, 2017.
U.S. Appl. No. 15/202,115, office action dated Sep. 26, 2016.
U.S. Appl. No. 15/225,428, office action dated Aug. 14, 2018.
U.S. Appl. No. 15/225,428, office action dated Dec. 20, 2017.
U.S. Appl. No. 15/225,504, office action dated Apr. 4, 2017.
U.S. Appl. No. 15/225,504, office action dated Aug. 1, 2018.
U.S. Appl. No. 15/225,504, office action dated Nov. 9, 2016.
U.S. Appl. No. 15/225,542, office action dated Apr. 4, 2017.
U.S. Appl. No. 15/225,542, office action dated Nov. 22, 2016.
U.S. Appl. No. 15/286,006, office action dated Jan. 9, 2017.
U.S. Appl. No. 15/286,006, office action dated Jan. 18, 2018.
U.S. Appl. No. 15/286,006, office action dated May 16, 2017.
U.S. Appl. No. 15/286,024, office action dated Jan. 6, 2017.
U.S. Appl. No. 15/286,024, office action dated May 19, 2017.
U.S. Appl. No. 15/331 754; office action dated Oct. 11, 2018.
U.S. Appl. No. 15/359,569, office action dated Feb. 22, 2017.
U.S. Appl. No. 15/359,569, office action dated Jun. 23, 2017.
U.S. Appl. No. 15/359,569, office action dated Jul. 12, 2018.
U.S. Appl. No. 15/412,554, office action dated Sep. 27, 2018.
U.S. Appl. No. 15/412,564, office action dated Jul. 10, 2018.
U.S. Appl. No. 15/412,596, office action dated Sep. 4, 2018.
U.S. Appl. No. 15/412,610, office action dated Jul. 9, 2018.
U.S. Appl. No. 15/413,257; office action dated Sep. 25, 2018.
U.S. Appl. No. 15/414,536, office action dated Oct. 11, 2018.
U.S. Appl. No. 15/452,669, office action dated May 5, 2017 .
U.S. Appl. No. 15/452,669, office action dated Nov. 16, 2017 .
Arakawa et al., "Protein-Solvent Interactions in Pharmaceutical Formulations", Pharm. Res., Mar. 1991, vol. 8, Issue 3, pp. 285-291.
Armitage et al., "New approach to classifying non-Hodgkin's lymphomas: clinical featorcs of the major histologic subtypes. Non-Hodgkin's Lymphoma Classification Project" J Clin Oncol 16, 2780-2795 (1998).
Asadullah et al., "Interleukin-10 therapy—review of a new approach", Pharmarcol Rev., 2003, 55(2):241-269.
Atkins et al., "High-dose recombinant interleukin-2 therapy in patients with metastatic melanoma: long-term survival update", Cancer J Sci Am., 2000, Suppl 6:SII-14.
Atkins, "Interieukin-2: clinical applications", Semin Oncol., 2002, 29(3 Suppl 7):12-27.
Avastin® Bevacizumab, Roche, [drug label], 24 pages, Sep. 2008.
Baba, Oleo Science 10(1):15-18 (Jan. 2010).
Bairagi et al., Albumin: A Versatile Drug Carrier, Austin Therapeutics, (Nov. 17, 2015) vol. 2, No. 2, p. 1021 (pp. 1-6).
Balch et al., "The new melanoma staging system", Semin Cutan Med Surg., 2003, 22(1):42-54.
Balch et al., "Update on the melanoma staging system: The importance of sentinel node staging and primary tumor mitotic rate", Journal of Surgical Oncology, Aug. 19, 2011, vol. 104, issue 4, pp. 379-385.
Bauer et al., "Rituximab, ofatumumab, and other monoclonal anti-CD20 antibodies for chronic lymphocytic leukaemial (Review)," Cochrane Database of Systematic Reviews, Issue 11, 125 pages (copyright 2012).
Baumgartner et al., "Melanoma induces immunosuppression by up-regulating FOXP3(+) regulatory T cells", J Surg Res., 2007, 141(1): 72-77.
Belani et al., "Multicenter, randomized trial for stage IIIB or IV non-small-cell lung cancer using weekly paclitaxel and carboplatin followed by maintenance weekly paclitaxel or observation", J. Clin. Oncol., 2003, 21:2933-2939.
Bird et al., "Single-chain antigen-binding proteins", Science, Oct. 1988, 242(4877), pp. 423-426.
Boasberg et al., "Nab-paditaxel and bevacizumad as first-line therapy in patients with unresectable stage III and IV nelanoma", J Clinical Oncology, 2009, 27, No. 15S, abstract #9071.
Boasberg et al., "Phase II trial of nab-paditaxel and bevacizumab as first-line therapy in patients with unresectable nelanoma", Journal of Clinical Oncology, May 20, 2011, vol. 29, No. 15 Supp, 8543.
Bolstad et al., "A comparison of normalization methods for high density oligonucleotide array data based on variance and bias", Bioinformatics, 2003, 19:185-193.
Cao et al., "Response of resistant melanoma to a combination of weekly paclitaxel and bevacizumab", Clin Transl Oncol, 2007, 9:119-120.
Carson et al. "A phase 2 trial of a recombinant humanized monoclonal anti-vascular endothelial growth factor (VEGF) antibody in patients with malignant melanoma", Proceedings of the ASCO vol. 22, No. 2873, General Poster Session, Thirty-Ninth Annual Meeting of the American Society of Clinical Oncology, May 31-Jun. 3, 2003, Chicago, IL, 2 pages.
Celis, "Overlapping human leukocyte antigen class I/II binding peptide vaccine for the treatment of patients with stage IV melanoma: evidence of systemic immune dysfunction", Cancer, 2007, 110(1):203-214.

(56) References Cited

OTHER PUBLICATIONS

Chapman et al., "Improved Survival with Vemurafenib in Melanoma with Braf V600E Mutation", The New England Journal of Medicine, Jun. 30, 2011, vol. 364, Issue 26, pp. 2507-2516.
Chisholm et al., "Response to influenza immunization during treatment for cancer", Arch Dis Child, 2001, 84(6):496-500.
Chong et al., "Combining cancer vaccines with chemotherapy", Expert Opin Pharmacother., 2006, 6(16):2813-2820.
Cleland et al., "The Development of Stable Protein Formulations: A close look at protein aggregation, deamidation, and oxidation", Therapeutic Drug Carrier Systems, 1993, 10(4), pp. 307-377.
Colman, "Effects of amino acid sequence changes on antibody-antigen interactions," Research in Immunology (145(1):33-36,(1994).
Davis, "Affinity separation of antibody-toxin conjugate from albumin-stabilized formulatian", Am Biotechnol Lab., 12(4):60-64, Mar. 1994.
Degrasse, "A Single-Stranded DNA Aptamer That Selectively Binds to *Staphylococcus aureus* Enterotoxin B", PLoS One, 2012, 7(3) e33410, pp. 1-7.
Deguchi et al., "Effect of Methotrexate-Monoclonal Anti-Prostatic Acid Phosphatase Antibody Conjugate on Human Prostate Tumor", Cancer Research, Aug. 1986, 46, pp. 3751-3755.
Demirkesen et al., "The correlation of angiogenesis with metastasis in primary cutaneous melanoma: a comparative analysis of microvesset density, expression of vascular endothelial growth factor and basic fibroblastic growth factor", Pathology, 2006, 38:132-137.
Denardo et al.. "Inflammation and breast cancer. Balancing immune response: crosstalk between adaptive and innate immune ceils during breast cancer progression", Breast Cancer Res., 2007, 9(4):212.
Desai et al., "Enhanced antitumor activity and safety of albumin-bound nab-docetaxel versus polysorbate 80-based docetaxel", Eur. J. Cancer, Suppl.; 18th Symposium on molecular targets and cancer therapeutics; Prague, Czech Republic; Nov. 7-10, 2006, vol. 4, No. 12, Nov. 2006 *Nov. 2006), p. 49.
Desai et al., "Increased antitumor activity, Intratumor paclitaxel concentrations, and endothelial cell transport of cremophor-free, albumin-bound paclitaxel, ABI-007, compared with cremophor-based paclitaxel", Clin Cancer Res., 2006, 12(4): 1317-24.
Deweers et al., "Daratumumab, a novel therapeutic human CD38 monoclonal antibody, induces killing of multiple myeloma and other hematological tumors", J. Immunol., 186(3); 1840-1848, Feb. 1, 2011.
Dudek et al., "Autologous large multivalent immunogen vaccine in patients with metastatic melanoma and renal cell carcinoma", Am, J. Ciin. Oncol., Apr. 1, 2008, 31(2):173-181.
Edison, "MorphoSys," 16 pages (Aug. 8, 2013).
Elbayoumi et al., "Tumor-Targeted Nanomedicines: Enhanced Antitumor Efficacy In vivo of Doxorubicin-Loaded, Long-Circulating Liposomes Modified with Cancer-Specific Monoclocal Antibody", Clin Cancer Res., 2009, 15(6):1973-1980.
Ellyard et al., "Th2-mediated anti-tumour immunity: friend or foe'?", Tissue Antigens, 2007, 70(1):1-11.
Elsadek et al., "Impact of albumin on druf delivery—New applications on the hoizon", J of Controlled Release, 2011, 1-25.
Emens et al.: "(OT1-01-06) A phase III randomized trial of alezolizumab in combination with nab-paclitaxel as firs tline therapy for patienst with metastatic triple-negative breast cancer (mTNBC)", 2015. XP002775313. 2015 San Antonio Breast Cancer Symposium, URL: http://sabcs.org/portals/sabcs2016/documents/sabcs-2015-abstracts.pdf?v=5.
European Application No. 08743903.0, Extended European Search Report dated Jan. 24, 2011.
European Application No. 09774506.1, Extended European Search Report dated Mar. 22, 2012.
European Application No. 12781802.9, Extended European Search Report dated Dec. 18, 2014.
European Application No. 13843209.1, Extended European Search Report dated Sep. 5, 2016.
European Application No. 15806443.6, Extended European Search Report dated Dec. 11, 2017.
European Application No. 15809075.3, Extended European Search Report dated Dec. 21, 2017.
Fabi et al, "Prospective study on nanoparticle albumin-bound paclitaael biological observations in advanced breast cancer: clinical results and biological observations in taxane-pretreated patients", Drug Design, Development and Therapy vol. 9, Nov. 1, 2015, 7 pages.
Ferrara et al., "The biology of VEGF and its receptors", Nat. Med., 2003, 9:669-676.
Flaherty et al., "Final Results of E2603: a double-blind, randomized phase III trial comparing carboplatin (C)/paclitaxel(P) with or without sorafenib(S) in metastatic melanoma", J. Clin Oncol., 2010, 28:15s (suppl: abstr 8511).
Flores et al., "Novel oral taxane therapies: recent Phase I results", Clin. Invest. vol. 3, No, 4, Apr. 1, 2013 (Apr. 1, 2013), pp. 333-341, XP055426571, UK, ISSN: 2041-6792, DOI: 10.4155/cli.13.18.
Folkman, "Angiogenesis in cancer, vascular, rheumatoid and other disease", Nat. Med., 1995, 1, 27-31.
Fricke et al., "Vascular endothelial growth factor-trap overcomes defects in dendritic cell differentiation but does not improve antigen-specific immune responses", Clin. Cancer Res., 2007, 13:4840-4848.
Gabrilovich et al., "Production of vascular endothelial growth factor by human tumors inhibits the functional maturation of dendrite cells", Nat. Med., 1996, 2: 1096-1103.
Gao et al., "In vivo cancer targeting and imaging with semiconductor quantum dots", Nat Biotech, 2004, 22(8):969-976.
Gogas et al., "Chemotherapy for metastatic melanoma: time for a change?", Cancer, 2007, 109(3): 455-464.
Golay et al., "Mechanism of notion of therapeutic monoclonal antibodies: promises and pitfalls of in vitro and in vivo assay," Arch. Biochem. Biophys. 526(2):146-153 (2012).
Graells et al., Overproduction or VEGF165 concomitantly expressed with its receptors promotes growth and survival of melanoma cells through MAPK and P13K signaling, J. Invest. Dermatol., 2004, 123:1151-1161.
Gupta et al "Ofatumumab, the first human anti-CD20 monoclonal antibody for the treatment of B cell hematologic malignancies," Ann. N.Y. Acad. Sci., (Jul. 25, 2012).
Haley et al., "Nanoparticles for drug delivery in cancer treatment", Urol. Oncol.: Seminars and Original Invest, 2008, 26:57-64.
Hamilton et al, "Nab-Paclitaxel/Bevadzurnab/Carboplatin Chemotherapy in First-Line Triple Negative Metastatic Breast Cancer", Clinical Breast Cancer, vol. 13, No. 6, Dec. 1, 2013, 6 pages.
Hara, "What is anti-HER2 antibody tubulin polymerization inhibitor complex T-DM1?," Pharm. Monthly 56(5):734-739 (May 2014).
Harlow et al., Antibodies: A Laboratory Manual, Cold Spring Harbor Laboratory, New York, 1988 (9 pages).
Hassan et al: "Comparison of Different Crosslinking Methods for Preparation of Docetaxel-loaded Albumin Nanoparticles", Iranian Journal of Pharmaceutical Research, vol. 14, No. 2, Apr. 2015 (Apr. 2015), pp. 385-394.
Hauschild et al., "Individualized therapy of disseminated cancer using malignant melanoma as a model", Cancer and Metastasis Reviews, 2006, 25(2): 253-256.
Hauschild et al., "Results of a Phase III, Randomized, Placebo-Controlled Study of Sorafenib in Combination with Carboplatin and Paclitaxel as Second-Line Treatment in Patients with Unresectable Stage III or Stage IV Melanoma", Journal of Clinical Oncology, Jun. 10, 2009, vol. 27, No. 17, pp. 2823-2830.
Hegde et al, "Predictive Impact of Circulating Vascular Endothelial Growth Factor in Four Phase III Trials Evaluating Bevacizumab," Clinical Cancer Research, Feb. 15, 2013 (Feb. 15, 2013) vol. 19, pp. 929-937.
Hersh et al., "A Phase 2 Clinical Trial of nab-Paclitaxel in Previously Treated and Chemotherapy-Naïve Patients With Metastatic Melanoma", Cancer, Jan. 1, 2010, 116:155, pp. 155-163.
Hersh at al., "A randomized, controlled phase III trial of nab-Paclitaxel versus dacarbazine in chemotherapy-naive patients with metastatic melanoma", Ann Oncol, 2015, epub Sep. 26, 2015.

(56) References Cited

OTHER PUBLICATIONS

Hersh et al., "Open-label. multicenter, phase II trial of ABI-007 in previously treated and previously untreated patients with metastatic malignant melanoma", J. Clin. Oncol., 2005, 23(16S):7558 (Abstract).
Hobbs et al., "Regulation of Transport pathways in tumor vessels: role of tumor type and microenvironment", Proc Watt Acad Sci USA, Apr. 1998, 95, pp. 4607-4612.
Hodi et al., "Improved survival with ipilimuab in patients with metastatic melanoma", The New England Journal of Medicine, Aug. 19, 2010, vol. 363. No. 8, pp. 711-723.
Hodi et al., "Phase II study of paclitaxel and carboplatin for malignant melanoma", Am. J. Clin. Oncol., 2002, 25:283-286.
Hood et al., Immunology, 1984, Benjamin, N.Y., 2nd edition.
Huncharek et al., "Single-agent DTIC versus combination chemotherapy with or without immunotherapy in metastatic melanoma: a meta-analysis of 3273 patients from 20 randomized trials", Melanoma Research, 11:75-81 (2001).
Hunkapiller et al., "Immunology: The growing immunoglobulin gene superfamily", Nature, Sep. 1986, 323, pp. 15-16.
Huston et al., "Protein engineering of antibody binding sites; Recovery of spedfic activity in an anti-digoxin single-chain Fv analogue produced in *Escherichia coli*", Proc. Natl. Acad. Sci. USA, Aug. 1988, vol. 85, pp. 5879-5883.
Ibrahim et al., "Phase I and Phamacokinetic Study of ABI-007, a Cremophor-free, Protein-stabilized, Nanoparticle Formulation of Paclitaxel", Clinical Cancer Research, May 2002, vol. 8, pp. 1038-1044.
Inagaki et al., "Clinical significance of serum Thl-, Th2- and regulatory T cells-associated cytokines in adult T-cell leukemia/lymphoma: High interleukin-5 and -10 levels are significant unfavorable prognostic factors", Int. J. Cancer, 2006, 118(12):3054-3061.
Inman, "Atezolizumab/Nab-Paclitaxel Combo Shows High Response Rates in TNBC", OneLive, Dec. 10, 2015, 4 pages.
International Preliminary Report on Patentability for Application No. PCT/US2008/057025, dated Sep. 15, 2009.
International Preliminary Report on Patentability for Application No. PCT/US2009/049511, dated Jan. 5, 2011.
International Preliminary Report on Patentability for Application No, PCT/US2012/037137, dated Nov. 12, 2013.
International Preliminary Report on Patentability for Application No. PCT/US2013/062638, dated Apr. 16, 2015.
International Preliminary Report on Patentability for Application No. PCT/US2015/035505, dated Dec. 22, 2016.
International Preliminary Report on Patentability for Application No. PCT/US2015/035515, dated Dec. 29, 2016.
International Preliminary Report on Patentability for Application No. PCT/US2015/054295 dated Oct. 13, 2016.
International Preliminary Report on Patentability for Application No. PCT/US2016/026270, dated Oct. 13, 2018.
International Preliminary Report on Patentability for Application No. PCT/US2017/023442, dated Oct. 4, 2018.
International Preliminary Report on Patentability for Application No. PCT/US2017/023443, dated Oct. 4. 2018
International Preliminary Report on Patentability for Application PCT/US2016/026267, dated Apr. 10, 2018.
International Preliminary Report on Patentability for Application PCT/US2017/017653, dated Aug. 23, 2018.
International Search Report and Written Opinion for Application No. PCT/US2008/057025, dated Jul. 1, 2008.
International Search Report and Written Opinion for Application No. PCT/US2009/049511, dated Feb. 2, 2010.
International Search Report and Written Opinion for Application No. PCl/US2012/037137, dated Sep. 28, 2012.
International Search Report and Written Opinion for Application No. PCT/US2013/062638, dated Jan. 23, 2014.
International Search Report and Written Opinion for Application No. PCT/US2015/035505, dated Nov. 24, 2015.
International Search Report and Written Opinion for Application No. PCT/US2015/035515, dated Sep. 21, 2015.
International Search Report and Written Opinion for Application No. PCT/US2015/054295, dated Jan. 25, 2016.
International Search Report and Written Opinion for Application No. PCT/US2016/026267, dated Jul. 12, 2016.
International Search Report and Written Opinion for Application No. PCT/US2016/026270, dated Oct. 12, 2017.
International Search Report and Written Opinion for Application No. PCT/US2016/047641, dated Oct. 31, 2016.
International Search Report and Written Opinion for Application No. PCT/US2017/017553, dated Feb. 10, 2017.
International Search Report and Written Opinion for Application No. PCT/US2017/023442, dated Jun. 16, 2017.
International Search Report and Written Opinion for Application No. PCT/US2017/023443, dated Jul. 11, 2017.
International Search Report and Written Opinion for Application No. PCT/US2017/049745, dated Oct. 25, 2017.
International Search Report and Written Opinion for Application No. PCT/US2017/049745, dated Dec. 15, 2017.
International Search Report and Written Opinion for Application No. PCT/US2017/049746, dated Nov. 27, 2017.
International Search Report and Written Opinion for Application No. PCT/US2017/050134, dated Nov. 16, 2017.
International Search Report and Written Opinion for Application No. PCT/US2017/050137, dated Nov. 27, 2017.
International Search Report and Written Opinion for Application No. PCT/US2017/050355 dated Jan. 30, 2018.
Jaime et al., "Pactitaxel antibody conjugatos and trehalose for preserving the immunological activity after freeze-drying," Curr Piled Chem, 2004, 11(4):439-46 Abstract Only.
Jain et al., "Delivering nanomedicine to solid tumors", Nature Reviews Clinical Oncology, Nov. 2010, 7, pp. 653-664.
Jain et al., "Normalizing tumor vasculature with anti-angiogenic therapy: a new paradigm for combination therapy," Nat. Med. 7(9):987-969 (2001).
Jain, "Normalization of tumor vasculature: an emerging concept in antiangiogenic therapy," Science 307(5706):58-62 (2005).
Jazirehi et al., "Rituximab (anti-CD20) selectively modifies Bcl-xl and apoptosis protease activating factor-1 (Apaf-1) expression and sensitizes human non-Hodgkin's lymphoma B cell lines to paciltaxel-induced apoptosis," Mol. Cancer Ther. 2(11):1183-93 (2003).
Jiang et al., "Regulation of Immune Responses by T Cells", N Engl J Med., 2006, 354(11): 1166-1176.
Jin et al., "Paclitaxel-loaded nanoparticies decorated with anti-CD133 antibody, atargeted therapy for liver cancer stem cells," J. Nanopart. Res. 2014, 16:2157 (2014).
Jin et al: "Docetaxel-loaded PEG-albumin nanoparticles with improved antitumor efficiency against non-small cell lung cancer", Oncology Reports vol. 36, No. 2, Aug. 8, 2016 (Aug. 8, 2016), pp. 871-876, XP055425487, ISSN: 1021-335X, DOI: 10.3892/or.2016.4863.
Julien et al, "Utilization of monoclonal antibody-targeted nanornaterials in the treatment of cancer", 2011, MAbs, 3:467-478.
Kamat et al., "Metronomic chemotherapy enhances the efficacy of antivascular therapy in ovarian cancer", Cancer Res., 2007, 67(1):281-288.
Kawai et al., "VEGF121 promotes lymphangiogenesis in the sentinel lymph nodes of non-small cell lung carcinoma patents", Lung Cancer, 2008, 59(1):41-47.
Kelly et al. "Shape-Specific, Monodisperse Nano-Molding of Protein Particles," J. Am. Chem. Soc. 130:5438-5439 (2008).
Kikuchi et al., "Vascular endothelial growth factor and dendritic cells in human squamous cell carcinoma of the oral cavity", Anticancer Res., 2006, 26(3A):1833-1848.
Kim et al. "A dual target-directed agent against interleukin-6 receptor and tumor necrosis factor a ameliorates experimental arthritis", Scientific Rep. 6:20150 (2016).
Kim et al., "BEAM: A Randomized Phase II Study Evaluating the Activity of Bevadzurriab in Combination with Carboplatin Plus Paclitaxel in Patients With Previously Untreated Advanced Melanoma", Journal of Clinical Oncoloy: official journal of the American Society of Clinical Oncology, Jan. 1, 2012, vol. 30, No, 1, pp. 34-41.
Kirkwood et al., "A pooled analysis of eastern cooperative oncology group and intergroup trials of adjuvant high-dose interferon for melanoma", Clin Cancer Res., 2004, 10(5): 1670-1677.

(56) References Cited

OTHER PUBLICATIONS

Kondejewski et al., "Synthesis and characterization of carbohydrate-linked murine monoclonal antibody K20-human seam albumin conjugates", Bioconjug Chem., 5(6):602-611, Nov.-Dec. 1994.
Korman et al., "Tumor immunotherapy: preclinical and clinical activity of anti-CTLA4 antibodies", Curr Opin Invest Drugs, 2005, 6(6):582-591.
Kottschade et al., "A Phase II Trial of Nab-Paclitaxel (ABI-007) and Carboplatin in Patients with Unresectable Stage IV Melanoma", Cancer, Apr. 15, 2011, 117(8), pp. 1704-1710.
Kottschade et al., "A Randomized Phase 2 Study of Ternozolomide and Bevacizumab or nab-Paclitaxel, Carboplatin, and Bevacizumab in Patients with Unresectable Stage IV Melanoma",Cancer, 2013, vol. 119, Issue 3, pp. 586-592.
Kratz et al, "Serum proteins as drug carriers of anticancer agents: a review", Drug Deliv., 5(4):281-299, 1998.
Kratz, "Albumin as a drug carrier: design of prodrugs, drug conjugates and nanoparticles", J Control Release, 132(3):171-183, Epub May 17, 2008.
Kukowska-Latallo et al., "Nanoparticle Targeting of Anticancer Drug improves Therapeutic Response in Animal Model of Human Epithelial Cancer", Cancer Res, 2005, 65(12):5317-5324.
Kumar et al., Th1/Th2 cytokine imbalance in meningioma, anaplastic astrocytoma and ghoblastoma multiforme patients, Oncol. Ran., 2006, 15(6):1513-1516.
Lanzavecchia et al., "The use of hybrid hybridomas to target human cytotoxic T lymphocytes", Eur. J. Immunol, 1987, 17, pp. 105-111.
Lau et al.,"Is inhibition of cancer angiogenesis and growth by paclitaxel schedule dependent?", Anti-Cancer Drugs, 2004, 15:871-875.
Lee et al., "The co-delivery of paclitaxel and Herceptin using cationic micellar nanoparticles", Biomaterials vol. 30, No. 5, Feb. 1, 2009, pp. 919-927.
Lei et al., "Comparing cellular uptake and cytotoxicity of targeted drug carriers in cancer cell lines with different drug resistance mechanisms", Nanomed: Nanotech, Biol, and Med., 2011, 7:324-332.
Lev et al., "Dacarbazine causes transcriptional up-regulation of interleukin 8 and vascular endothelial growth factor in melanoma cells: a possible escape from chemotherapy", Mol. Cancer Ther., 2003, 2:753-763.
Lev et al., "Exposure of melanoma cells to dacarbazine results in enhanced tumor growth and metastasis in vivo", J. Clin. Oncol., 2004, 22:2092-2100.
Lundin et al., "Phase 2 study of alemtuzumab (anti-CD52 monoclonal antibody) in patients with advanced mycosis fungoides/Sezary syndrome", Blood (2003) vol. 101, No. 11, pp. 4267-4272.
Marcoval et al., "Angiogenesis and malignant melanoma. Angiogenesis is related to the development of vertical (tumorigenic) growth phase", J. Cutan. Pathol., 1997, 24:212-218.
Markovic et al, "A phase II study of ABT-510 (thrombospondin-1 analog) for the treatment of metastatic melanoma", Am. J. Clin. Oncol., 2007, 30(3):303-309.
Markovic et al., "A reproducible method for the enumeration of functional (cytokine producing) versus non-functional peptide-specific cytotoxic T lymphocytes in human peripheral blood", Clin. Exo. Immunol., 2006, 145:438-447.
Markovic et al., "Peptide vaccination of patients with metastatic melanoma: improved clinical outcome in patients demonstrating effective immunization", Am J Clin Oncol., 2006, 29(4):352-360.
Matejtschuk, "Lyophilization of Proteins", Methods in Molecular Biology. Cryopreservation and Freeze-Drying Protocols, Second Edition, Edited by: J.G. Day and G.N. Stacey. Humane Press Inc., Totowa, NJ, 2007, vol. 368, pp. 59-72.
Matsuda et al., Preoperative oral immune-enhancing nutritional supplementation corrects TH1/TH2 imbalance in patients undergoing elective surgery for colorectal cancer, Dis. Colon Rectum, 2006, 49(4):507-516.
Mayo Clinic, "Paclitaxel Alburnin-Stabilized Nanoparticle Formulation and Bevacizumab in Treating Patients With Stage IV Melanoma That Cannot Be Removed by Surgery", Dec. 19, 2013, ClinicalTrials.gov., URL: https://www.clinicaltrials.gov/ct2/show/NCT02020707 (Four (4) pages).
McElroy et al., "Imaging of Primary and Metastatic Pancreatic Cancer Using a Fiuorophore-Coniugated Anti-CA19-9 Antibody for Surgical Navigation", World J Surg., 2008, 32: 1057-1066.
Meadows et at. "Anti-VEGF Therapies in the Clinic," Cold Spring Harbor Perspectives in Medicine, Oct. 1, 2012 (Oct. 1, 2012), vol. 2, pp. 1-27.
Melcher, "Recommendations for influenza and pneumococcal vaccinations in people receiving chemotherapy", Clin Oncol (R Coll Radian), 2005. 17(1): 12-15.
Merchan et al., "Increased endothelial uptake of paclitaxel as a potential mechanism for its antiangiogenic effects: potentiation by Cox-2 inhibition", Int. J. Cancer, 2005, 113, pp. 490-498.
Mezzaroba et al., "New potential therapeutic approach for the treatment of B-Cell malignancies using chlorambucil/Hydroxychloroquine-Loaded Anti-CD20 Nanoparticles", PLoS One vol. No. 8, Issue 9 pp. 1-10, e74215.
Middleton et al., "Randomized phase III study of temozolomide versus dacarbazine in the treatment of patients advanced metastatic malignant melanoma", J. Clin. Oncol., 2000; pp. 158-166.
Miller et al., "Paclitaxel plus Bevacizumab versus Paclitaxel Alone for Metastatic Breast Cancer," N Engl. J Med., (2007) vol. 357:2666-2676.
Mimura et al., Vascular endothelial growth factor inhibits the function of human mature dendritic cells mediated by VEGF receptor-2, Cancer Immunol Immunother., 2007, 56(6), pp. 761-770.
Mirtsching et al., "A Phase II Study of Weekly Nanoparticie Albumin-Bound Paclitaxel With or Without Trastuzumab in Metastatic Breast Cancer", Clinical Breast Cancer, 2011, 11(2):121-128.
Mocellin et al., "Cytokines and immune response in the tumor microenvironment", J Immunother., 2001, 24(5), pp. 392-407.
Motl, "Bevacizumab in combination chemotherapy for colorectal and other cancers", Am. J. Health-Svst. Pharm 2005, 62, pp. 1021-1032.
Mustacchi et al, "The role of taxanes in triple-negative breast cancer: literature review", Drug Design, Development and Therapy, vol. 9, Aug. 6, 2015, 16 pages.
Nahleh et al, "Swog S0800 (NCI CDR0000636131) addition of bevacizumba to neoadjuvant nab-paclitaxel with dose-dense doxorubidn and cyclophosphamide improves pathologic complete response (pCR) rates in inflammatory or locally advanced breast cancer", Breast Cancer Research and Treatment, vol. 158, No. 3 Jul. 8, 2016, 12 pages.
Nevala et al, "Abstract B77: Targeted nano-immune conjugates to melanoma: Predinical testing of bevacizumab targeted nab-paclitaxel", Cancer Immunology Research, vol. 3, Oct. 1, 2015, 3 pages.
Nevala et al, "Antibody-targeted paditaxel loaded nanoparticles for the treatment of CD20 B-cell lymphoma", Scientific Reports, vol. 7, Apr. 5, 2017, 9 pages.
Nevala et al "Antibody-Targeted Chemotherapy for the Treatment of Melanoma", Cancer Research, vol. 76, No. 13, Jul. 1. 2016, pp. 3954-3964
Nevala et al, "Targeted nano-immune conjugates to melanoma: Preblinical testing of bevacizumab targeted nab-paclitaxel", Proceedings of the AACR Special Conference: Tumor Immunology and Immunotherapy: A New Chapter, Dec. 1, 2014, 2 pages.
Ng et al., "Influence of formulation vehicle on metronomic taxane chemotherapy: albumin-bound versus cremophor EL-based paclitaxel", Clin. Cancer Res., 2006, 12, pp. 4331-4338.
Ng et al., "Taxane-mediated antiangiogenesis in vitro: influence of formulation vehicles and binding proteins", Cancer Res., 2004, 64, pp. 821-824.
Nilvebrant et al., "The Albumin-Binding Domain as a Scaffold for Protein Engineering", Computational and Structural Biotechnology Journal, Mar. 2013, vol. 6, Issue 7, e201303099, http://dx.doi.org/10.5936/csbj.201303099.
Nishida et al, English Translation of "Clinical Trials of New Drugs Cytotoxic Effect against Multiple Myeloma with High Expression

(56) References Cited

OTHER PUBLICATIONS of a CD38 Antigen and a Human CD38 Monoclonal Antibody Daraturnurnab:CD36 Antigen", history of Medicine, Sep. 29, 2012, vol. 242. No. 13, pp. 1176-1181.

Oku et al., "Tumor growth modulation by sense and antisense vascular endothelial growth factor gene expression: effects on angiagenesis, vascular permeability, blood volume, blood flow, fluorodeoxyglucose uptake, and proliferation of human melanoma intracerebral xenografts", Cancer Res., 1998, 58, pp. 4185-4192.

Ouichi, Antibody delivery—from basics to clinical test—"Clinical development of antibody-drug conjugate," Drug Deliv. Sys. 28(5):424-429 (2013).

Parikh et al., "The vascular endothelial growth factor family and its receptors", Hematol. Oncol Clin. N. Am., 2004. 18, pp. 951-971.

Park et al., "Anti-HER2 Immunoliposomes. Enhanced Efficacy Attributable to Targeted Delivery", Clin. Cancer Res., 2002, 8, pp. 1172-1181.

Parker et al., "Targeting CLL, Cells Using Rituximab-Conjugated Surface Enhanced Raman Scattering (SERS) Gold Nanoparticles," Blood vol. 116, No. 21. Nov. 1, 2010, pp. 1109.

Perez et al,. "Phase 2 Trial of Carboplatin, Weekly Paclitaxel, and Biweekly Bevacizumab in Patients with Unresectable Stage IV Melanoma", Cancer, 2009, vol. 115, Issue 1, pp. 119-127.

Petrelli et al., "Targeted Delivery for Breast Cancer Therapy: the History of Nanoparticle-Albumin-Sound Paclitaxel," Expert Opinion on Pharmacotherapy, Jun. 1, 2010 (Jun. 1, 2010), vol. 11, pp. 1413-1432.

Pikal., "Freeze-drying of proteins, Part II: Formulation selection"; Biopharm, 1990, 9, pp. 26-30.

Polak et al., "Mechanisms of local immunosuppression in cutaneous melanoma", Br J Cancer. 2007, 96(12), pp. 1879-1867.

Porrata et al.; "Early lymphocyte recovery predicts superior survival after autologous hematopoletic stem cell transplantation in multiple myeloma or non-Hodgkin lymphoma", Blood, 2001, 98(3), pp. 579-585.

Porrata et al., "Timely reconstitution of Immune competence affects clinical outcome following autologous stem cell transplantation", Clin Exp Med., 2004, 4(2):78-85.

Powell et at., "Adoptive transfer of vaccine-induced peripheral blood mononuclear cells to patients with metastatic melanoma following lymphodepletion", J Immunol., 2006, 177(9), pp. 6527-6539.

Pries et al., "Cytokines in head and neck cancer", Cytokine Growth Factor Rev., 2006, 17(3), pp. 141-146.

Qu Na et al: "Cabazitaxel-loaded human serum albumin nanoparticles as a therapeutic agent against prostate cancer", International Journal of Nanomedicine, vol. 11, Jul. 26, 2016 (Jul. 26, 2016), pp. 3451-3459.

Ranieri et al., "Vascular endothelial growth factor (VEGF) as a target of bevacizumab in cancer: from the biology to the clinic", Curr. Med. Chem., 2006, 13, 1845-1857.

Rao at al., "Combination of Paolitaxel and Carboplatin as Second-Line Therapy for Patients with Metastatic Melanoma", Cancer, Jan. 16, 2006, vol. 106, No. 2, pp. 375-382.

Ribas et al., "Antitumor melanoma and anti-self responses in a phase I trial with the anti-cytotoxic T lymphocyte-associated antigen 4 monoclonal antibody CP-675,206", J Clin Oncol., Dec. 10, 2005, 23(35), pp. 8968-8977.

Rosenberg et al., "Tumor progression can occur despite the induction of very high levels of self/tumor antigen-specific CD8+ T cells in patients with melanoma", J. lmmunol., 2005, 175(9), pp. 6169-6176.

Roy et al., "Tumor associated release responsiveness of interleukin-10 alters the prolactin receptor and down—regulates prolactin responsiveness of immature cortical thermocytes", J Neuroimmunol., 2007, 186(1-2), pp. 112-120.

Rudikoff et al., "Single amino acid substitution altering antigen-binding specificity," Proc Natl Acad Sci USA 1982 vol. 79 pp. 1979-1983.

Rudnicka et al., "Rituximab causes a polarization of B cells that augments its therapeutic function in NK-cell-mediated antibody-dependent cellular cytotoxicity", Blood, 2013, 121(23):4694-4702.

Sadat et al., "Nano-pharmaceutical Formulations for Targeted Drug Delivery against HER2 in Breast Cancer", Current Cancer Drug Targets, 2015, 15(1):71-85.

Salven et al., "Enhanced expression of vascular endothelial growth factor in metastatic melanoma", Br. J. Cancer, 1997, 76(7), pp. 930-934.

Samaranayake et al., "Modified taxols. 5.1 Reaction of taxol with electrophilic reagents and preparation of a rearranged taxol derivative with tubulin assembly activity", J. Org. Chem., vol. 56, 1991, pp. 5114-5119.

Sandler et al., "Paclitaxel-carboplatin alone or with bevacizumab for non-small-cell lung cancer", N. Engl. J. Med., 2006, 355:2542-2550.

Sato et al., "Intraepithelial CD8+ tumor-infiltrating lymphocytes and a high CD8+/regutatory T cell ratio are associated with favorable prognosis in ovarian cancer", Proc Nati Acad Sci USA, 2005, 102(51):18538-18543.

Schrama et al. "Antibody targeted drugs as cancer therapeutics", Nature Reviews 5:147-159 (2006).

Sester et al., "Differences in CMV-specific T-cell levels and long-term susceptibility to CMV infection after kidney, heart and lung transplantation", Am J Transplant., 5(6),1483-1489, Jun. 2005.

Soda et al., Latest topics of new medicine "Albumin-bound paclitaxel," Mol. Respiratory Dis. 17(1):100-103 (Mar. 1, 2013).

Srivastava et al., "Angiogenesis in cutaneous melanoma: pathogenesis and clinical implication", Microsc. Res. Tech., 2003, 60:208-224.

Stancovski et al., "Mechanistic aspects of the opposing effects of monoclonal antivodies to the ERBB2 receptor on tumor growth," Proc Natl Acad Sci USA, 88: 8691-8695, (1991).

Streit et al., "Angiogenesis, lymphangiogenesis, and melanoma metastasis", Oncogene, 2003, 22, pp. 3172-3179.

Taieb et al., "Chemoimmunotherapy of tumors: Cyclophosphamide synergtizes with exoxome based vaccines", J. Immunol., Mar. 1, 2006, 176(5):2722-2729.

Tao et al., "Inhibiting the growth of malignant melanoma by blocking the expression of vascular endothelial growth factor using an RNA interference approach", Br. J. Dermatol., 2005, 153:715-724.

Tas et al., "Circulating serum levels of angiogenic factors and vascular endothelial growth factor receptors 1 and 2 in melanoma patients", Melanoma Res., 2006, 16:405-411.

Terheyden et al., "Anti-vascular endothelial growth factor antibody bevacizumab in conjunction with chemotherapy in metastasizing melanoma", J Cancer Res Clin Oncol, 2007, 133(11), pp. 897-901.

Terui, English Translation of Molecular-Targeted Therapy for Cancer. Progresses and Challenges, "Daratumumab, Antibody Drug against Myeloma", Pharma Med., Nov. 10, 2013, vol. 31, No. 11, p. 27-30.

Ugurel et al., "Increased serum concentration of angiogenic factors in malignant melanoma patients correlates with tumor progression and survival", J. Clin. Oncol., 2001, 19:577-583.

Vacca et al., "Docetaxel versus paclitaxel for antiangiogenesis", J. Hematother. Stem Cell Res., 2002, 11:103-118.

Varker et al., "A randomized phase 2 trial of bevacizumab with or without daily low-dose interferon alfa-2b in metastatic malignant melanoma", Ann Surg Oncol., 14(8):2367-2378, print Aug 2007, Epub May 2007.

Vence et al., "Circulating tumor antigen-specific regulatory T cells in patients with metastatic melanoma", Proc Natl Acad Sci USA, 2007, 104(52). pp. 20884-20889.

Vishnu et al., "Safety and Efficacy of nab-Paclitaxel in the Treatment of Patients with Breast cancer," Breast Cancer. Basic and Clinical Research. 2011. vol. 5, pp. 53-65.

Volk et al., "Nab-paclitaxel efficacy in the orthotopic model of human breast cancer is significantly enhanced by concurrent anti-vascular endothelial growth factor A therapy," Neoplasia 10(6):613-623 (2008).

(56) References Cited

OTHER PUBLICATIONS

Volk-Draper et al, "Novel Model Therapy for Basaloid Triple-negative Breast Cancer Behavior In Vivo and Response to Therapy", vol. 14, No. 10, Oct. 1, 2012, 18 pages.
Wagner et al., "Enhanced drug targeting by attachment of an anti alphav integrin antibody loaded human serum albumin nanoparticles", Biomaterials 31(8):2388-2398, Epub Dec. 23, 2009.
Walker et al., "Monitoring immune responses in cancer patients receiving tumor vaccines", Int Rev Immunol., 2003; 22(3-4):283-319.
Wang et al., "Biofunctionalized targeted nanoparticles for therapeutic applications", Expert Opin. Biol. Thor., 2008, 8(8): 1063-1070.
Wang et al., "Paciitaxel at ultra low concentrations inhibits angiogenesis without affecting cellular microtubule assembly", Anti-Cancer Drugs, 2003, vol. 14, Issue 1, pp. 13-19.
Washington University School of Medicine "Phase I/II Study of Abraxane in Recurrent and Refractory Lymphoma", ClinicalTrials.gov, Dec. 6, 2016, 7 pages.
Weber, "Review: anti-CTLA-4 antibody ipilimumab: case studies of clinical response and immune-related adverse events", Oncologist, Jul. 2007, 12(7), pp. 864-872.
Wiernik et al., "Phase I trial of taxol given as a 24-hour infusion every 21 days: responses observed in metastatic melanoma", Journal of Clinical Oncology, Aug. 1987, vol. 5, No. 8, pp. 1232-1239.
Wong et al., "Programmed death-1 blockade enhances expansion and functional capacity of human melanoma antigen-specific CTLs", Int. Immunol., 2007, vol. 19, No. 10, pp. 1223-1234.
Wu et al., "Aptamers Active Targeting Ligands for Cancer Diagnosis and Therapy", Theranostics, 2015, 5(4):322-344.
Yardley et al., "A pilot study of adjuvant nanoparticle albumin-bound (nab) paclitaxel and cyclophosphamide, with trastuzumab in HER2-positive patients, in the treatment of early-stage breast cancer", Breast Cancer Res Treat, 2010, 123:471-475.
Yee et al., "Adoptive T cell therapy using antigen-specific CD8+ T cell clones for the treatment of patients with metastatic melanoma: In vivo persistence, migration, and antitumor effect of transferred T cells", Proc Natl Acad Sci USA, 2002, 99(25):16168-16173.
Yu et al., "Interaction between bevaclzumab and murine VEGF-A: a reassessment," Invest. Ophthatmol. Visual Sci. 49(2): 522-527, Feb. 2008.
Yuan et al., "Vascular Permeability in a Human Tumor Xenograft: Molecular Size Dependence and Cutoff Size", Cancer Research, Sep. 1, 1995, 55, pp. 3752-3756.
Yuan et al., "Time-dependent vascular regression and permeability changes in established human tumor xenografts induced by an anti-vascular endothelial growth factor/vascular permeability factor antibody," Proc. Natl. Acad. Sci. USA 93(25):14765-14770 (1996).
Zimpfer-Rechner et al., "Randomized phase II study of weekly paclitaxel versus paclitaxel and carboplatin as second-line therapy in disseminated melanoma: a multicentre trial of the Dermatologic Co-operative Oncology Group (DeCOG)", Melanoma Res., 2003, 13:531-536.
U.S. Appl. No. 14/432,979, office action dated Jan. 7, 2019.
U.S. Appl. No. 15/052,336, office action dated Jan. 22, 2019.
U.S. Appl. No. 15/052,623, office action action Jan. 7, 2019.
U.S. Appl. No. 15/092,433; office action dated Dec. 12, 2018.
U.S. Appl. No. 15/187,672, office action dated Nov. 28, 2018.
U.S. Appl. No. 15/331,754; office action dated Feb. 22, 2019.
U.S. Appl. No. 15/412,536; office action dated Oct. 1, 2018.
U.S. Appl. No. 15/412,581; office action dated Nov. 13, 2018.
Application No. 15/412,596, office action dated Dec. 27, 2018.
U.S. Appl. No. 15/414,526; office action dated Nov. 16, 2018.
U.S. Appl. No. 15/414,533; office action dated Nov. 19, 2018.
U.S. Appl. No. 151452,689, office action dated Nov. 26, 2018.
Elst et al, "Epidermal Growth Factor Receptor Expression and Activity in Acute Myeloid Leukemia", Blood 116:3144 (2010), abstract.
Lin, "Salmon Calcitonin: Conformational Changes and Stabilizer Effects", AIMS Biophysics, 2015, 2(4): 695-723.

Lloyd et al, "Modelling the human immune response: performance of a 1011 human antibody repertoire against a broad panel of therapeutically relevant antigens", Protein Eng., Design & Selection 22(3):159-168 (2009).
Anonymous, "Phase I/II Study of Abraxane in Recurrent and Refractory Lymphoma", NCT01555853: ClinicalTrials.gov, Jun. 6, 2014 (8 pages).
U.S. Appl. No. 15/092,403, office action dated May 23, 2019.
U.S. Appl. No. 15/092,433, office action dated May 30, 2019.
U.S. Appl. No. 15/225,542; office action dated Jul. 18, 2019.
U.S. Appl. No. 15/412,581, office action dated Mar. 8, 2019.
U.S. Appl. No. 15/412,610, office action dated Mar. 14, 2019.
U.S. Appl. No. 15/414,526; office action dated Mar. 12, 2019.
U.S. Appl. No. 15/414,533; office action dated Mar. 8, 2019.
U.S. Appl. No. 15/430,411, office action dated May 1, 2019.
U.S. Appl. No. 15/452,669; office action dated Jun. 24, 2019.
U.S. Appl. No. 15/456,377; office action dated Mar. 19, 2019.
U.S. Appl. No. 15/456,377; office action dated Jul. 5, 2019.
U.S. Appl. No. 15/456,382; office action dated Jul. 8, 2019.
U.S. Appl. No. 15/456,395; office action dated Mar. 28, 2019.
U.S. Appl. No. 15/456,399; office action dated Mar. 28, 2019.
U.S. Appl. No. 15/456,382; office action dated Mar. 18, 2019.
U.S. Appl. No. 15/456,391; office action dated Mar. 15, 2019.
U.S. Appl. No. 15/460,552; office action ated Apr. 1, 2019.
U.S. Appl. No. 15/460,699; office action dated Mar. 28, 2019.
U.S. Appl. No. 15/461,288; office action dated Apr. 1, 2019.
Bedu-Addo "Understanding Lyophilization Formulation Development", Pharmaceutical Technology Lyophilization. pp. 10-18 (2004).
Beers et al. "CD20 as a Target for Therapeutic Type I and II Monoclonal Antibodies", Seminars in Hematology 47(2):107-114 (2010).
Cheng et al. Molecularly targeted drugs for metastatic colorectal cancer. Drug Des Devel Ther. Nov. 1, 2013;7: 1315-22 (Year: 2013).
Coiffier "The Role of Rituximab in Lymphomas", Rev. Bras. Hematol. Hemoter., 2002, vol. 24, No. 3, ISSN: 1516-8484 (6 pages).
Edwards et al. The Remarkable Flexibility of the Human Antibody Repertoire; Isolation of Over One Thousand Different Antibodies to a Single Protein, BLyS, J. Mol. Biol 334:103-118 (2003).
European Application No. 16837869.3, Extended European Search Report dated Apr. 4, 2019.
International Preliminary Report on Patentability for Application No. PCT/US2017/045643, dated Feb. 14, 2019.
International Preliminary Report on Patentability for Application No. PCT/US2017/049745, dated Mar. 14, 2019.
International Preliminary Report on Patentability for Application No. PCT/US2017/049746, dated Mar. 14, 2019.
International Preliminary Report on Patentability for Application No. PCT/US2017/050137 dated Mar. 21, 2019.
Iqbal et al. Anti-Cancer Actions of Denosurnab. Curr Osteoporos Rep. Dec. 2011;9(4): 173-6. (Year: 2011).
Krishnan et al., "Programmed death-1 receptor and interleukin-10 in liver transplant recipients at high risk for late cytomegalovirus disease", Transpl Infect Dis., 12(4):363-70, print Aug 2010, ePub Jan 2010.
Mattnay et al. Promising therapeutic targets in neuroblastoma. Clin Cancer Res. May 15, 2012;18(10):2740-53, (Year: 2012).
Package Insert, Campath® (ALEMTUZUMAB), Millennium and ILEX Partners, LP, 13 pages, available May 2001.
Reck et al. "Ipilimumab in combination with paclitaxel and carboplatin as first-line therapy in extensive-disease-small-cell lung cancer results from a randomized, double-blind, multicenter phase 2 trial", Ann Oncol 24(1):75-83 (2013).
Robak, T. Emerging monoclonal antibodies and related agents for the treatment of chronic lymphocytic leukemia. Future Oncol. Jan. 2013;9(1):69-91. Abstract Only. (Year: 2013).
Verma et at. "Effect of surface properties on nanoparticle-cell interactions", Small. 6(1): 12-21. (2010).
European Application No. 17736453.6, Extended European Search Report dated Jul. 8, 2019.
Khallouf et al. "5-Fluorouracil and Interferon-alpha Immunochemotherapy Enhances Immunogenicity of Murine Pan-

(56) References Cited

OTHER PUBLICATIONS creatic Cancer Through Upregulation of NKG2D Ligands and MHC Class 1", Immunother 35(3):245-253 (2012).
Korthals et al. "Monocyte derived dendritic cells generated by IFN-alpha acquire mature dendritic and natural killer cell properties as shown by gene expression analysis", J Translated Medicine 5:46 (2007) (11 pages).
Belldegrun et al. "Human Renal Carcinoma Line Transfected with Interleukin-2 and/or Interferon alpha Gene(s): Implications for Live Cancer Vaccines", J Natonal Cancer Institute 85(3):207-216 (1993).
Buechner "Intralesional interferon alfa-2b in the treatment of basal cell carcinoma", J Am Acad Dermatol 24:731-734 (1991).
Doveil et al. "Adjuvant Therapy of Stage IIIb Melanoma with Interferon Alta-2b:Clinical and Immunological Relevance", Dermatology 191:234-239 (1995).
U.S. Appl. No. 16/456,391; office action dated Jul. 24, 2019.

\* cited by examiner

METHODS OF TREATING CANCER WITH INTERFERON WHEREIN THE CANCER CELLS ARE HLA NEGATIVE OR HAVE REDUCED HLA EXPRESSION

CROSS REFERENCE TO RELATED APPLICATIONS

This application is a 35 U.S.C. § 371 national phase application of PCT Application PCT/US2017/012580 filed Jan. 6, 2017, which claims priority under 35 U.S.C. § 119(e) to U.S. Provisional Application No. 62/276,198, filed Jan. 7, 2016, the entire contents of each of which are incorporated herein by reference in its entirety.

FIELD

This disclosure relates to novel methods for treating cancer in a patient having a plurality of Human Leukocyte Antigen ("HLA")-negative cancer cells or cancer cells with reduced HLA expression by using Interferon-alpha in an amount sufficient to expand and/or activate immune cells, e.g., mature killer cells, to kill the HLA-negative cancer cells or the cancer cells with reduced HLA expression.

BACKGROUND

The therapeutic efficacy of conventional cancer treatments, including chemotherapy, surgery, and radiotherapy, are limited for a large number of cancers. For example, chemotherapeutic agents are generally considered ineffective in treating brain metastases from solid tumors because the drugs cannot penetrate the intact blood brain barrier.

Moreover, chemotherapeutic agents may cause considerable side effects on healthy cells in patients. Allen T M. (2002) *Cancer* 2:750-763. Further, cancer recurrence in cancer patients is often associated with surgery and radiotherapy, which can lead to higher mortalities in cancer patients. Clarke M, et al. (2005) *Lancet* 366 (9503):2087-106.

Cancer immunotherapy has emerged as an important therapy for cancers, particularly for advanced and refractory cancers. Compared to the conventional therapies, immunotherapy demonstrates great potential for cancer treatment with significantly higher specificity and efficacy. Since immunotherapy uses the patients' own immune system to destroy cancer cells, it has little or no side effects that are often associated with traditional treatment. The use of genetically modified T-cells for cancer treatment is one of the most noted cancer immunotherapies. Couzin-Frankel J. (2013) *Science* 20342(6165):1432-3. Activated cancer-specific T-cells can kill cancer cells by recognizing the specific antigens or peptides expressed on the cells.

Therefore, there remains a need in the art to develop a novel cancer immunotherapy with improved efficacy.

SUMMARY

A drawback of certain T-cell based cancer therapies is that cancer cells can develop escape mechanisms to evade the course of immunotherapy, particularly the immunotherapy directed by cancer-specific T-cells. Embodiments of the technology herein generally is predicated, at least in part, on the discovery that a patient having a plurality of HLA-negative cancer cells or cancer cells with reduced HLA expression can be effectively treated with interferon-alpha ("IFN-alpha") in an amount sufficient to expand and/or activate immune cells such that the activated and/or expanded immune cells kill one or more of HLA-negative cancer cells or the cancer cells with reduced HLA expression. In one embodiment, the immune cells can be T-cells, B-cells, or NK cells. In another embodiment, the patient is HLA-negative or has reduced expression of a class I HLA, a class II HLA, or a class III HLA. Preferably, the HLA is class I HLA or class II HLA.

In one aspect of the invention, IFN-alpha can be one or more of IFN-alpha 1, IFN-alpha 2, IFN-alpha 4, IFN-alpha 5, IFN-alpha 6, IFN-alpha 7, IFN-alpha 8, IFN-alpha 10, IFN-alpha 14, IFN-alpha 16, IFN-alpha 17, or IFN-alpha 21. Preferably, IFN-alpha is IFN-alpha 2, IFN-alpha 8, or IFN-alpha 10. In other preferred embodiments, the IFN-alpha is IFN-alpha 8. In one embodiment, IFN-alpha is a synthetic or recombinant IFN-alpha.

In one aspect of the invention, the effective amount of the IFN-alpha is a sub-therapeutic amount of the IFN-alpha. It is contemplated that administration of a sub-therapeutic amount of IFN-alpha can still activate, or expand the immune cells, including NK cells, such that the activated and/or expanded immune cells can kill one or more of HLA-negative cancer cells or cancer cells with reduced HLA expression. In one embodiment, the amount of IFN-alpha is sub-therapeutic compared to an amount of IFN-alpha that is used to treat a cancer. In one embodiment, the sub-therapeutic amount of IFN-alpha can be about 1%, about 5%, about 10%, about 15%, about 20%, about 25%, about 30%, about 35%, about 40%, about 45%, about 50%, about 55%, or about 60% of a therapeutic dosage of the IFN-alpha. In another embodiment, the IFN-alpha is provided in an amount ranging from about $5 \times 10^1$ units per square meter of body surface (U/m$^2$) to about $2 \times 10^5$ U/m2, or any sub value or sub range therein. Administration of a sub-therapeutic amount of IFN-alpha allows for greater targeting of the immune cells (e.g., NK cells) to the tumor, or decreasing any potential side effects associated with IFN-alpha, or both.

In one embodiment, to expand, activate, and/or stimulate the immune cells, the IFN-alpha can be administered orally, via vein injection, muscle injection, peritoneal injection, subcutaneous injection, nasal or mucosal administration, or by inhalation via an inspiratory.

In one aspect of the invention, the cancer comprises a population of cancer cells that initially express an HLA prior to comprising a population that is HLA-negative or have a reduced HLA expression. In one embodiment, the patient has received or is selected based upon having received an immunotherapy for the cancer. In one embodiment, the immunotherapy is a T-cell therapy.

In one embodiment, the IFN-alpha is administered as part of a combination therapy. In another embodiment, the combination therapy comprises one or more of chemotherapy, radiotherapy, and immunotherapy.

One aspect of the invention relates to a method for treating a cancer, which comprises administering an immune cell to a subject in need thereof, wherein said immune cell is activated by IFN-alpha, further wherein the cancer has no or reduced expression of a HLA compared to a normal control. In one embodiment, the immune cell is a T-cell, a B-cell, or a NK-cell. Preferably, the immune cell is a NK cell. In one embodiment, the NK cell is a NK cell line, e.g., a NK-92 cell.

In one embodiment, the HLA is a class I HLA antigen, a class II HLA antigen, or a class III HLA antigen. Preferably, the HLA is a class I HLA antigen or a class II HLA antigen.

In another embodiment, the source of the immune cells is autologous, allogeneic, or xenographic.

In one embodiment, the immune cells are administered intravenously, intraperitoneally, intramuscularly, or subcutaneously.

In one embodiment, the immune cells, such as NK cells, are activated by incubating the immune cells with the IFN-alpha ex vivo. In another embodiment, the immune cells are incubated ex vivo with the IFN-alpha at a concentration from $5 \times 10^1$ U/$1 \times 10^6$ cells to $1 \times 10^4$ U/$1 \times 10^6$ cells.

In one embodiment, the immune cells, such as NK cells, are administered in combination with an anti-tumor agent. In another embodiment, the anti-tumor agent is a chemotherapy agent, a radiotherapy agent, or an immunotherapy agent, such as an anti-cancer vaccine, an anti-cancer antibody, or an immune checkpoint inhibitor.

In one embodiment, the immune cell is modified to express a tumor cell homing receptor on the outer cell surface of the immune cell. In another embodiment, the tumor cell homing receptor is a chimeric antigen receptor, an Fc receptor, or combinations thereof.

In one embodiment, the patient or subject is human.

In one embodiment is provided a composition comprising immune cells and an effective amount of interferon alpha (IFN-alpha) to activate the immune cells.

In one embodiment, the IFN-alpha comprises one or more of IFN-alpha 1, IFN-alpha 2, IFN-alpha 4, IFN-alpha 5, IFN-alpha 6, IFN-alpha 7, IFN-alpha 8, IFN-alpha 10, IFN-alpha 14, IFN-alpha 16, IFN-alpha 17, or IFN-alpha 21.

In one embodiment, the immune cells are NK cells. In one embodiment, the NK cells are NK-92 cells.

In one embodiment, the composition comprises IFN-alpha at a concentration from 5×101 U/1×106 cells to 1×104 U/1×106 cells.

In one embodiment, the composition further comprises a pharmaceutically acceptable excipient.

DETAILED DESCRIPTION

After reading this description, it will become apparent to one skilled in the art how to implement the invention in various alternative embodiments and alternative applications. However, not all embodiments of the present invention are described herein. It will be understood that the embodiments presented here are presented by way of an example only, and are not limited. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

Throughout this disclosure, various publications, patents and published patent specifications are referenced by an identifying citation. The disclosures of these publications, patents and published patent specifications are hereby incorporated by reference in their entirety into the present disclosure.

Definitions

Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely examples and that equivalents of such are known in the art.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or sub value there between. Preferably, the term "about" when used with regard to a dose amount means that the dose may vary by +/−10%.

The term "comprising" or "comprises" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

The terms "patient," "subject," "individual," and the like are used interchangeably herein, and refer to any animal, or cells thereof whether in vitro or in situ, amenable to the methods described herein. In a preferred embodiment, the patient, subject, or individual is a mammal. In some embodiments, the mammal is a mouse, a rat, a guinea pig, a non-human primate, a dog, a cat, or a domesticated animal (e.g. horse, cow, pig, goat, sheep). In especially preferred embodiments, the patient, subject or individual is a human.

The term "treating" or "treatment" covers the treatment of a disease or disorder described herein, in a subject, such as a human, and includes: (i) inhibiting a disease or disorder, i.e., arresting its development; (ii) relieving a disease or disorder, i.e., causing regression of the disease or disorder; (iii) slowing progression of the disease or disorder; and/or (iv) inhibiting, relieving, or slowing progression of one or more symptoms of the disease or disorder. For example, treatment of a cancer or tumor includes, but is not limited to, reduction in size of the tumor, elimination of the tumor and/or metastases thereof, remission of the cancer, inhibition of metastasis of the tumor, reduction or elimination of at least one symptom of the cancer, and the like.

The term "administering" or "administration" of an agent, drug, or an immune cell, including but not limited to a natural killer cell, to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

It is also to be appreciated that the various modes of treatment or prevention of medical diseases and conditions as described are intended to mean "substantial," which includes total but also less than total treatment or prevention, and wherein some biologically or medically relevant result is achieved.

As used herein, the term "effective amount" refers to an amount of IFN-alpha which is capable of activating the immune cells. The precise effective amount will vary, for example based on the type of the immune cells to be activated and the subtype of IFN-alpha administered.

As used herein, the term "sub-therapeutic amount" is used to describe an amount of IFN-alpha that is below the amount of IFN-alpha conventionally used to treat a cancer. For example, a sub-therapeutic amount is an amount less than that defined by the manufacturer as being required for therapy. For example, in some non-limiting embodiments, a sub-therapeutic amount of IFN-alpha can be an amount less than $2 \times 10^7$ U/m$^2$, including any sub value or subrange below that amount and above $5 \times 10^1$ U/m$^2$. Other non-limiting examples of a sub-therapeutic amounts include those described in Ningram, R A (2014) *Scientifica* Volume 2014, Article ID 970315, and references cited within, each of which is incorporated herein by reference in its entirety.

As used herein, the term "therapeutic amount" refers to an amount of IFN-alpha conventionally used to treat a cancer. A "therapeutic amount" can be any amount defined by the manufacturer as being required for therapy. The therapeutic amount of the IFN will vary depending on the tumor being treated and its severity as well as the age, weight, etc., of the patient to be treated. For example, for hairy cell leukemia, the therapeutic amount for IFN-alpha 2b is $2 \times 10^6$ U/m$^2$; for malignant melanoma, the therapeutic amount is $2 \times 10^7$ U/m$^2$. The skilled artisan will be able to determine appropriate dosages depending on these and other factors. The compositions can also be administered in combination with one or more additional therapeutic compounds. In the methods described herein, the therapeutic compounds may be administered to a subject having one or more signs or symptoms of a disease or disorder.

As used herein, the term "interferon" or "IFN" means the family of highly homologous species-specific proteins that inhibit viral replication and cellular proliferation and modulate immune response.

The terms "α-interferon," "alpha interferon," "interferon alpha" and "human leukocyte interferon" are used interchangeably in this application to describe members of this group. Both naturally occurring and recombinant α-interferons, including consensus interferon, may be used in the practice of the invention.

As used to describe the present invention, "natural killer cells" or "NK cells" are cells of the immune system that kill target cells in the absence of a specific antigenic stimulus, and without restriction according to MHC class. Target cells may be tumor cells or cells harboring viruses. NK cells are characterized by the presence of CD56 and the absence of CD3 surface markers.

As used to describe the present invention, the terms "cytotoxic" and "cytolytic," when used to describe the activity of effector cells such as NK cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK cells is due to cytolysis.

The term "ex vivo" as used herein means that in vitro expansion, activation, and/or stimulation of immune cells, including T-cells, B-cells, and NK cells, prior to introducing the expanded, activated, and/or stimulated immune cells to a subject or a patient.

The term "therapeutic" as used herein means a treatment and/or prophylaxis. A therapeutic effect is obtained by suppression, remission, or eradication of a disease state.

As used herein, "endogenous" refers to any material from or produced inside an organism, cell, tissue or system.

As used herein, the term "exogenous" refers to any material introduced from or produced outside an organism, cell, tissue or system.

The term "human leukocyte antigens" or "HLA," refers to proteins (antigens) found on the surface of white blood cells and other tissues that are responsible for regulation of the immune system. HLA includes class I, class II, and class III HLA molecules.

The term "kill" with respect to a cell/cell population is directed to include any type of manipulation that will lead to the death of that cell/cell population.

"Antibodies" as used herein include polyclonal, monoclonal, single chain, chimeric, humanized and human antibodies, prepared according to conventional methodology.

"Cytokine" is a generic term for non-antibody, soluble proteins which are released from one cell subpopulation and which act as intercellular mediators, for example, in the generation or regulation of an immune response. See Human Cytokines: Handbook for Basic & Clinical Research (Aggarwal, et al. eds., *Blackwell Scientific*, Boston, Mass. 1991) (which is hereby incorporated by reference in its entirety for all purposes).

"Immune cells" as used herein are cells of hematopoietic origin that are involved in the specific recognition of antigens. Immune cells include antigen presenting cells (APCs), such as dendritic cells or macrophages, B-cells, T-cells, natural killer cells, etc.

The term "anti-cancer therapy" as used herein refers to cancer treatments, including but not limited to, chemotherapy and radiotherapy, as well as immunotherapy and vaccine therapy.

As used herein, "chimeric antigen receptors" or "CARs" refer to fusion proteins comprised of an antigen recognition moiety and immune cell activation domains. Eshhar et al., (1993) *Proc. Natl. Acad. Sci.*, 90(2): 720-724. For example, a CAR is an artificially constructed hybrid protein or polypeptide containing an antigen binding domain of an antibody (e.g., a single chain variable fragment (scFv)) linked to T-cell signaling or T-cell activation domains. CARs have the ability to redirect T-cell specificity and reactivity toward a selected target (i.e., a tumor cell) in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein (e.g., a CAR). The expression product itself, e.g. the resulting protein, may also be said to be "expressed." An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to an ES cell or pronucleus, so that the cell will express the introduced gene or sequence to produce a desired substance in a genetically modified animal.

The term "reduced expression" in reference to HLA expression means a decrease in HLA on the surface of a cancer cell. For example, reduced expression can be about 1.5 times, or alternatively, about 2.0 times, or alternatively, about 2.5 times, or alternatively, about 3.0 times, or alternatively, about 5 times, or alternatively, about 10 times, or alternatively about 50 times, or yet further alternatively more than about 100 times lower expression than the expression level detected in a control sample (e.g. an earlier cancer biopsy, compared to expression on typical cancer cells of the type, or on NK cells). The control sample also can be cells collected from a person not having cancer.

Overview

The current invention is predicated, in part, on the surprising discovery that treatment of a cancer expressing no or reduced HLA antigen with immune cells activated by IFN-alpha, either in vivo or ex vivo, provides for unexpectedly improved therapeutic outcomes.

As will be apparent to the skilled artisan upon reading this disclosure, the present disclosure relates to methods for treating a patient suffering from a cancer expressing no or reduced HLA antigen by treating the patient with immune cells, e.g., NK cells, which are activated by an effective amount or a sub-therapeutic amount of IFN-alpha.

Immune Cells and Immunotherapy

Immune cells are part of the complex network that defends the body against pathogens and other foreign substances, including cancer cells. The cells of the immune system include B-cells, dendritic cells, granulocytes, innate lymphoid cells (ILCs), megakaryocytes, monocytes/macrophages, natural killer (NK) cells, and T-cells, among others. The innate immune response, which is carried out by phagocytic cells (e.g., macrophages and cytotoxic NK cells) is the first line of defense to pathogenic exposure. Subsequently, the adaptive immune response includes antigen-specific defense mechanisms orchestrated by antigen-presenting cells (e.g., macrophages and dendritic cells).

Immunotherapy, including antibody and immune cell-based therapy, has emerged as a standard treatments for a number of cancers. Adoptive cell transfer ("ACT"), being tested for the treatment of cancer and chronic infections, has the potential to enhance antitumor immunity, augment vaccine efficacy, and limit graft-versus-host disease. In ACT, immune cells from the patient are modified and engineered ex vivo to recognize and attack the patient's own tumor. For adoptive T cell therapy, the modifications include altering the specificity of the T cell receptor (TCR) or introducing antibody-like recognition in chimeric antigen receptors (CARs).

At present, however, while immunotherapy has demonstrated in numerous experimental models as having considerable effectiveness, the clinical results have been less promising. One explanation is that tumors use many strategies to evade the host immune response, including down-regulation or weak immunogenicity of target antigens and creation of an immune-suppressive tumor environment. T-cell mediated immunotherapy requires that T-cells recognize and interact with a plurality of cell surfaces molecules, including HLA, and peptides. The interaction of T-cell and complexes of HLA/peptide is restricted, requiring a T-cell specific for a particular combination of an HLA molecule and a peptide. If the specific complex is lacking (e.g., does not express) one particular HLA, there is no T-cell response even if the T-cell is present. This mechanism is involved in the immune system's response to foreign materials, in autoimmune pathologies, and in responses to cellular abnormalities. Studies have shown that tumor cells develop various escape mechanisms to evade the T-cell-mediated immunotherapy. In one such escape mechanism, a cancer cell population which originally expressed a normal level of HLA on the cell surface reduces or eliminates the expression of HLA class I and/or HLA class II within the cancer cell population. The absence of HLA or the reduction of HLA expression impairs the recognition of cancer cells by T-cells and thus reduces subsequent cell lysis mediated by T-cells.

NK cells are at the core of innate immunity and can respond rapidly to viral infection or tumor formation by mediating the lysis of tumor cells and virally infected cells via natural cytotoxicity and antibody-dependent cellular cytotoxicity ("ADCC"). While a typical immune cell requires recognition of the major histocompatibility complex ("MHC") or HLA on the cell surface before triggering cytolytic responses, NK cells may recognize the infected cells or tumor in the absence of HLA on the cell surface. This unique feature of NK cells renders NK cells suitable for targeting those cancer cells with no or reduced HLA expression.

In one embodiment, a patient having a plurality of HLA-negative cancer cells or cancer cells with reduced HLA expression is treated with IFN-alpha in an amount sufficient to expand and/or activate immune cells such that the activated and/or expanded immune cells kill one or more of HLA-negative cancer cells or the cancer cells with reduced HLA expression. In another embodiment, a sufficient amount, or a sub-therapeutic amount of IFN-alpha can expand and/or activate the endogenous immune cells, including, but not limited to, NK cells in a host.

In another embodiment, NK cells can be expanded or activated ex vivo by IFN-alpha before they are administered back to the host to kill the HLA-negative cancer cells or the cancer cells with reduced expression of HLA compared to a normal control. NK cells can be administered to an individual by absolute numbers of cells; e.g., said individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) NK cells per injection, or any ranges between any two of the numbers, end points inclusive. In other embodiments, the amount of NK cells injected per dose may be calculated by $m^2$ of body surface area, including $1\times10^{11}$, $1\times10^{10}$, $1\times10^9$, $1\times10^8$, $1\times10^7$ (and so forth) NK cells per $m^2$. The average person is 1.6-1.8 $m^2$. In other embodiments, said individual can be administered from about 1000 cells/injection/m² to up to about 10 billion cells/injection/m², such as at about, at least about, or at most about, $1\times10^8$/m², $1\times10^7$/m², $5\times10^7$/m², $1\times10^6$/m², $5\times10^6$/m², $1\times10^5$/m², $5\times10^5$/m², $1\times10^4$/m², $5\times10^4$/m², $1\times10^3$/m², $5\times10^3$/m² (and so forth) NK cells per injection, or any ranges between any two of the numbers, end points inclusive. In other embodiments, NK-92 cells can be administered to such an individual by relative numbers of cells; e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) NK cells per kilogram of the individual, or any ranges between any two of the numbers, end points inclusive.

The immune cells of the present disclosure can be isolated from any source. In some embodiments, the source of the immune cells is autologous, allogeneic, or xenographic, or combinations thereof. The immune cells may be prepared ex vivo by extracting or otherwise isolating autologous immune cells from blood, bone marrow, or other immune cell-containing organs of a patient having a cancerous tumor or other cancer, according to methods known in the art. For example, such methods include, but are not intended to be limited to, apheresis techniques, specifically leukapheresis. In another embodiment of the invention, the NK cells can be autologous or allogeneic NK cells. "Autologous" NK cells are cells derived from the patient. "Allogeneic" NK cells are derived from another individual, having non-identical genes at one or more loci. If the NK cells are derived from an identical twin, they may be termed "syngeneic." Additionally, commercially available kits may be utilized for the extraction of NK cells, such as with EasySep™ Human NK Cell Isolation Kit available from STEMCELL™ Technologies, Inc., British Columbia, CANADA.

Natural Killer (NK) Cells

Natural killer (NK) cells are a class of lymphocytes that typically comprise approximately 10% of the lymphocytes in a human. NK cells provide an innate cellular immune response against tumor and infected (target) cells. NK cells, which are characterized as having a CD3-/CD56+ phenotype, display a variety of activating and inhibitory cell surface receptors. NK cell inhibitory receptors predominantly engage with major histocompatibility complex class I ("MHC-I") proteins on the surface of a normal cell to prevent NK cell activation. The MHC-I molecules define cells as "belonging" to a particular individual. It is thought that NK cells can be activated only by cells on which these "self" MHC-I molecules are missing or defective, such as is often the case for tumor or virus-infected cells.

NK cells are triggered to exert a cytotoxic effect directly against a target cell upon binding or ligation of an activating NK cell receptor to the corresponding ligand on the target cell. The cytotoxic effect is mediated by secretion of a variety of cytokines by the NK cells, which in turn stimulate and recruit other immune system agents to act against the target.

Activated NK cells also lyse target cells via the secretion of the enzymes perforin and granzyme, stimulation of apoptosis-initiating receptors, and other mechanisms.

NK cells have been evaluated as an immunotherapeutic agent in the treatment of certain cancers. NK cells used for this purpose may be autologous or non-autologous (i.e., from a donor).

In one embodiment, the NK cells used in the compositions and methods herein are autologous NK cells. In one embodiment, the NK cells used in the compositions and methods herein are non-autologous NK cells.

In one embodiment, the NK cells used in the compositions and methods herein are genetically modified NK cells. NK cells can be genetically modified by insertion of genes or RNA into the cells such that the cells express one or more proteins that are not expressed by wild type NK cells. In one embodiment, the NK cells are genetically modified to express a chimeric antigen receptor (CAR). In a preferred embodiment, the CAR is specific for the cancer being targeted by the method or composition.

Non-limiting examples of modified NK cells can be found, for example, in Glienke, et al. 2015, Advantages and applications of CAR-expressing natural killer cells, *Frontiers in Pharmacol.* 6, article 21; PCT Patent Pub. Nos. WO 2013154760 and WO 2014055668; each of which is incorporated herein by reference in its entirety.

In some embodiments, the NK cells are an NK cell line. NK cell lines include, without limitation, NK-92, NK-YS, KHYG-1, NKL, NKG, SNK-6, and IMC-1. See, Klingemann et al. Front Immunol. 2016; 7: 91, which is incorporated herein by reference in its entirety.

NK-92 Cells

The NK-92 cell line was discovered in the blood of a subject suffering from a non-Hodgkins lymphoma. NK-92 cells lack the major inhibitory receptors that are displayed by normal NK cells, but retain a majority of the activating receptors. NK-92 cells are cytotoxic to a significantly broader spectrum of tumor and infected cell types than are NK cells and often exhibit higher levels of cytotoxicity toward these targets. NK-92 cells do not, however, attack normal cells, nor do they elicit an immune rejection response. In addition, NK-92 cells can be readily and stably grown and maintained in continuous cell culture and, thus, can be prepared in large quantities under c-GMP compliant quality control. This combination of characteristics has resulted in NK-92 being entered into presently on-going clinical trials for the treatment of multiple types of cancers.

NK-92 cells used in the compositions and methods described herein may be wild type (i.e., not genetically modified) NK-92 cells or genetically modified NK-92 cells. NK-92 cells can be genetically modified by insertion of genes or RNA into the cells such that the cells express one or more proteins that are not expressed by wild type NK-92 cells. In one embodiment, NK-92 cells are genetically modified to express a chimeric antigen receptor (CAR) on the cell surface. In a preferred embodiment, the CAR is specific for the cancer being targeted by the method or composition. In one embodiment, NK-92 cells are genetically modified to express an Fc receptor on the cell surface. In a preferred embodiment, the NK-92 cell expressing the Fc receptor can mediate antibody-dependent cell-mediated cytotoxicity (ADCC). In one embodiment, the Fc receptor is CD16. In one embodiment, NK-92 cells are genetically modified to express a cytokine (e.g., IL-2).

In one embodiment, the modified NK-92 cell is administered in combination with an antibody specific for the cancer to be treated. In a preferred embodiment, the modified NK-92 cell administered in combination with the antibody is competent to mediate ADCC. Examples of NK-92 cells are available from the American Type Culture Collection (ATCC) as ATCC CRL-2407.

Non-limiting examples of modified NK-92 cells are described, for example, in U.S. Pat. Nos. 7,618,817 and 8,034,332; and U.S. Patent Pub. Nos. 2002/0068044 and 2008/0247990, each of which is incorporated herein by reference in its entirety. Examples of modified NK-92 cells are available from ATCC as ATCC CRL-2408, ATCC CRL-2409, PTA-6670, PTA-6967, PTA-8837, and PTA-8836. Non-limiting examples of CAR-modified NK-92 cells can be found, for example, in Glienke, et al. 2015, Advantages and applications of CAR-expressing natural killer cells, *Frontiers in Pharmacol.* 6, article 21; which is incorporated herein by reference in its entirety.

Interferon

Interferons ("IFNs") have long been recognized for their roles in regulating the immune response to infection inflammation and tumor formation. Human interferons are grouped into three classes based on their cellular origin and antigenicity: α-interferon (leukocytes), β-interferon (fibroblasts) and γ-interferon (B-cells). Recombinant forms of each group have been developed and are commercially available. Subtypes in each group are based on antigenic/structural characteristics. There are at least 24 IFN alpha subtypes identified so far, including IFN-alpha 1, IFN-alpha 2, IFN-alpha 4, IFN-alpha 5, IFN-alpha 6, IFN-alpha 7, IFN-alpha 8, IFN-alpha 10, IFN-alpha 14, IFN-alpha 16, IFN-alpha 17, or IFN-alpha 21. Among them, IFN-α1, IFN-α2, IFN-α8, IFN-α10, IFN-α14 and IFN-α21 are the major subtypes of IFN-alphas. In one embodiment, the IFN-alpha is IFN-alpha 1, IFN-alpha 2, IFN-alpha 4, IFN-alpha 5, IFN-alpha 6, IFN-alpha 7, IFN-alpha 8, IFN-alpha 10, IFN-alpha 14, IFN-alpha 16, IFN-alpha 17, or IFN-alpha 21. In another embodiment, IFN-alpha is IFN-alpha 2, IFN-alpha 8, or IFN-alpha 10. In other preferred embodiments, the IFN-alpha is IFN-alpha 8.

IFNs, e.g., IFN-alphas, can enhance immune cell cytotoxicity, migration, and cytokine production and inhibit tumor growth. The conditions that can be treated with IFNs include, but are not limited to, cell proliferation disorders, in particular cancer (e.g., hairy cell leukemia, Kaposi's sarcoma, chronic myelogenous leukemia, multiple myeloma, basal cell carcinoma and malignant melanoma, ovarian cancer, cutaneous T-cell lymphoma), and viral infections. Viral infections which may be treated in accordance with the invention include hepatitis A, hepatitis B, hepatitis C, other non-A/non-B hepatitis, herpes virus, Epstein-Barr virus (EBV), cytomegalovirus (CMV), herpes simplex, human herpes virus type 6 (HHV-6)), papilloma, poxvirus, picornavirus, adenovirus, rhinovirus, human T lymphotropic virus-type 1 and 2 (HTLV-1/-2), human rotavirus, rabies, retroviruses including human immunodeficiency virus (HIV), encephalitis and respiratory viral infections.

A number of immune cells can be stimulated, activated, and expanded by IFNs. For example, IFNs can enhance the cytotoxic activities of NK lymphocytes, which is critical for the primary innate immune system against viral and bacterial infections and tumorigenesis. Markovic S N et al (1991) *Cancer Research*, 51:1124. Moreover, the tumor cells from the IFN receptor-deficient animal models are unresponsive to the NK-mediated cell lysis. Swann J B, et al (2007) *J of Immun*, 178 (12):7540-7549. Therefore, the IFNs, including IFN-alpha, may be critical for controlling NK cell-mediated antitumor responses.

In one embodiment, a sufficient amount, or a sub-therapeutic amount of IFN-alpha can expand and/or activate the endogenous immune cells, including but not limited to NK cells in a host. The amount of IFN-alpha injected per dose may be calculated by square meter ($m^2$) of body surface area, including $1 \times 10^7$, $1 \times 10^6$, $1 \times 10^5$, $1 \times 10^4$, $1 \times 10^3$, $1 \times 10^2$ (and so forth) unitsper $m^2$ ($U/m^2$). The average person is 1.6-1.8 $m^2$.

In other embodiments, said individual can be administered from about 100 units/injection/$m^2$ to up to about 10 million units/injection/$m^2$, such as at about, at least about, or at most about, $1 \times 10^7$ $U/m^2$, $1 \times 10^6$ $U/m^2$, $1 \times 10^5$ $U/m^2$, $1 \times 10^4$ $U/m^2$, $1 \times 10^3$ $U/m^2$, $1 \times 10^2$ $U/m^2$ (and so forth) IFN-alpha per injection, or any ranges between any two of the numbers, end points inclusive. In other embodiments, said individual can be administered at about, at least about, or at most about, $5 \times 10^6$ $U/m^2$, $5 \times 10^5$ $U/m^2$, $5 \times 10^4$ $U/m^2$, $5 \times 10^3$ $U/m^2$, $5 \times 10^2$ $U/m^2$ (and so forth) IFN-alpha per injection, or any ranges between any two of the numbers, end points inclusive.

In one embodiment, the sub-therapeutic amount of the IFN-alpha is about 1%, about 5%, about 10%, about 15%, about 20%, about 25%, about 30%, about 35%, about 40%, about 45%, about 50%, about 55%, or about 60% of a therapeutic dosage of the IFN-alpha, or any ranges between any two of the numbers, end points inclusive. In another embodiment, the IFN-alpha is provided in an amount ranging from about $5 \times 10^1$ $U/m^2$ to about $2 \times 10^5$ $U/m^2$.

The amount of IFN-alpha used to expand and/or activate immune cells ex vivo can be calculated by the number of cells. The concentration of IFN-alpha for the ex vivo incubation of immune cells, e.g. NK cells, can be about $1 \times 10^1$ $U/1 \times 10^6$ cells to $1 \times 10^6$ $U/1 \times 10^6$ cell, such as at about, at least about, or at most about, $1 \times 10^8$ $U/1 \times 10^6$ cells, $1 \times 10^7$ $U/1 \times 10^6$ cells, $5 \times 10^7$ $U/1 \times 10^6$ cells, $1 \times 10^6$ $U/1 \times 10^6$ cells, $5 \times 10^6$ $U/1 \times 10^6$ cells, $1 \times 10^5$ $U/1 \times 10^6$ cells, $5 \times 10^5$ $U/1 \times 10^6$ cells, $1 \times 10^4$ $U/1 \times 10^6$ cells, $5 \times 10^4$ $U/1 \times 10^6$ cells, $1 \times 10^3$ $U/1 \times 10^6$ cells, $5 \times 10^3$ $U/1 \times 10^6$ cells, $1 \times 10^2$ $U/1 \times 10^6$ cells, $5 \times 10^2$ $U/1 \times 10^6$ cells, $1 \times 10^1$ $U/1 \times 10^6$ cells, $5 \times 10^1$ $U/1 \times 10^6$ cells (and so forth), or any ranges between any two of the numbers, end points inclusive. In one embodiment, the NK cells are incubated ex vivo with the IFN-alpha at a concentration from $5 \times 10^1$ $U/1 \times 10^6$ cells to $1 \times 10^4$ $U/1 \times 10^6$ cells.

Homing Receptor

In some embodiments, the immune cells are modified to express a tumor cell homing receptor on the outer cell surface of the immune cell. The homing receptor may be, for example, a chimeric antigen receptor, an Fc receptor, or combinations thereof. In some embodiments the CAR targets a cancer-associated antigen. In other embodiments, at least a portion of the immune cells express an endogenous tumor cell homing receptor that is not CXCR4.

In one aspect of the disclosure, the immune cell is modified to express a chimeric antigen receptor (CAR). In some embodiments, the immune cell is transformed with a nucleic acid encoding a CAR, wherein the CAR is expressed on the outer cell surface of the immune cell. In some embodiments, the immune cell is a T-cell, for example, an activated T-cell.

Any CAR known to one of skill in the art now or in the future is encompassed by the present disclosure. In one embodiment, the CAR is specific for a tumor-specific antigen. Tumor-specific antigens can also be referred to as cancer-specific antigen. In one embodiment, the CAR is specific for a tumor-associated antigen. Tumor-associated antigens can also be referred to as cancer-associated antigen. A tumor-specific antigen is a protein or other molecule that is unique to cancer cells, while a tumor-associated antigen is an antigen that is highly correlated with certain tumor cells and typically are found at higher levels on a tumor cell as compared to on a normal cell. Tumor-specific antigens are described, by way of non-limiting example, in U.S. Pat. Nos. 8,399,645; 7,098,008; WO 1999/024566; WO 2000/020460; and WO 2011/163401, each of which is incorporated herein by reference in its entirety. In addition, examples of some known CARs are disclosure in Table 2. In one embodiment, the CAR targets a tumor-associated antigen selected from the group consisting of α-folate receptor, CAIX, CD19, CD20, CD30, CD33, CEA, EGP-2, erb-B2, erb-B 2,3,4, FBP, GD2, GD3, Her2/neu, IL-13R-a2, k-light chain, LeY, MAGE-A1, Mesothelin, and PSMA.

In some embodiments, the CAR recognizes an antigen associated with a specific cancer type selected from the group consisting of ovarian cancer, renal cell carcinoma, B-cell malignancies, Acute lymphoblastic leukemia (ALL), chronic lymphocytic leukemia (CLL), B-cell malignancies, refractory follicular lymphoma, mantle cell lymphoma, indolent B-cell lymphoma, acute myeloid leukemia (AML), Hodgkin lymphoma, cervical carcinoma, breast cancer, colorectal cancer, prostate cancer, neuroblastoma, melanoma, rhabdomyosarcoma, medulloblastoma, adenocarcinomas, and tumor neovasculature.

TABLE 2

Chimeric Antigen Receptors

| Target antigen | Associated malignancy | Receptor type | CARs generation |
| --- | --- | --- | --- |
| α-Folate receptor | Ovarian cancer | ScFv-FcεRIγCAIX | First |
| CAIX | Renal cell carcinoma | ScFv-FcεRIγ | First |
| CAIX | Renal cell carcinoma | ScFv-FcεRIγ | Second |
| CD19 | B-cell malignancies | ScFv-CD3ζ (EBV) | First |
| CD19 | B-cell malignancies, CLL | ScFv-CD3ζ | First |
| CD19 | B-ALL | ScFv-CD28-CD3ζ | Second |
| CD19 | ALL | CD3ζ(EBV) | First |
| CD19 | ALL post-HSCT | ScFv-CD28-CD3ζ | Second |
| CD19 | Leukemia, lymphoma, CLL | ScFv-CD28-CD3ζ vs. CD3ζ | First and Second |
| CD19 | B-cell malignancies | ScFv-CD28-CD3ζ | Second |
| CD19 | B-cell malignancies post-HSCT | ScFv-CD28-CD3ζ | Second |
| CD19 | Refractory Follicular Lymphoma | ScFv-CD3ζ | First |
| CD19 | B-NHL | ScFv-CD3ζ | First |
| CD19 | B-lineage lymphoid malignancies post-UCBT | ScFv-CD28-CD3ζ | Second |
| CD19 | CLL, B-NHL | ScFv-CD28-CD3ζ | Second |
| CD19 | B-cell malignancies, CLL, B-NHL | ScFv-CD28-CD3ζ | Second |
| CD19 | ALL, lymphoma | ScFv-41BB-CD3ζ vs CD3ζ | First and Second |
| CD19 | ALL | ScFv-41BB-CD3ζ | Second |
| CD19 | B-cell malignancies | ScFv-CD3ζ (Influenza MP-1) | First |
| CD19 | B-cell malignancies | ScFv-CD3ζ (VZV) | First |
| CD20 | Lymphomas | ScFv-CD28-CD3ζ | Second |
| CD20 | B-cell malignancies | ScFv-CD4-CD3ζ | Second |
| CD20 | B-cell lymphomas | ScFv-CD3ζ | First |
| CD20 | Mantle cell lymphoma | ScFv-CD3ζ | First |
| CD20 | Mantle cell lymphoma, indolent B-NHL | CD3 ζ/CD137/CD28 | Third |
| CD20 | indolent B cell lymphomas | ScFv-CD28-CD3ζ | Second |
| CD20 | Indolent B cell lymphomas | ScFv-CD28-41BB-CD3ζ | Third |
| CD22 | B-cell malignancies | ScFV-CD4-CD3ζ | Second |
| CD30 | Lymphomas | ScFv-FcεRIγ | First |
| CD30 | Hodgkin lymphoma | ScFv-CD3ζ (EBV) | First |
| CD33 | AML | ScFv-CD28-CD3ζ | Second |
| CD33 | AML | ScFv-41BB-CD3ζ | Second |
| CD44v7/8 | Cervical carcinoma | ScFv-CD8-CD3ζ | Second |
| CEA | Breast cancer | ScFv-CD28-CD3ζ | Second |
| CEA | Colorectal cancer | ScFv-CD3ζ | First |
| CEA | Colorectal cancer | ScFv-FcεRIγ | First |
| CEA | Colorectal cancer | ScFv-CD3ζ | First |
| CEA | Colorectal cancer | ScFv-CD28-CD3ζ | Second |
| CEA | Colorectal cancer | ScFv-CD28-CD3ζ | Second |
| EGP-2 | Multiple malignancies | scFv-CD3ζ | First |
| EGP-2 | Multiple malignancies | scFv-FcεRIγ | First |
| EGP-40 | Colorectal cancer | scFv-FcεRIγ | First |
| erb-B2 | Colorectal cancer | CD28/4-1BB-CD3ζ | Third |
| erb-B2 | Breast and others | ScFv-CD28-CD3ζ | Second |
| erb-B2 | Breast and others | ScFv-CD28-CD3ζ (Influenza) | Second |
| erb-B2 | Breast and others | ScFv-CD28mut-CD3ζ | Second |
| erb-B2 | Prostate cancer | ScFv-FcεRIγ | First |
| erb-B 2,3,4 | Breast and others | Heregulin-CD3ζ | Second |
| erb-B 2,3,4 | Breast and others | ScFv-CD3ζ | First |
| FBP | Ovarian cancer | ScFv-FcεRIγ | First |
| FBP | Ovarian cancer | ScFv-FcεRIγ (alloantigen) | First |
| Fetal acetylcholine receptor | Rhabdomyosarcoma | ScFv-CD3ζ | First |

TABLE 2-continued

Chimeric Antigen Receptors

| Target antigen | Associated malignancy | Receptor type | CARs generation |
|---|---|---|---|
| GD2 | Neuroblastoma | ScFv-CD28 | First |
| GD2 | Neuroblastoma | ScFv-CD3ζ | First |
| GD2 | Neuroblastoma | ScFv-CD3ζ | First |
| GD2 | Neuroblastoma | ScFv-CD28-OX40-CD3ζ | Third |
| GD2 | Neuroblastoma | ScFv-CD3ζ (VZV) | First |
| GD3 | Melanoma | ScFv-CD3ζ | First |
| GD3 | Melanoma | ScFv-CD3ζ | First |
| Her2/neu | Medulloblastoma | ScFv-CD3ζ | First |
| Her2/neu | Lung malignancy | ScFv-CD28-CD3ζ | Second |
| Her2/neu | Advanced osteosarcoma | ScFv-CD28-CD3ζ | Second |
| Her2/neu | Glioblastoma | ScFv-CD28-CD3ζ | Second |
| IL-13R-a2 | Glioma | IL-13-CD28-4-1BB-CD3ζ | Third |
| IL-13R-a2 | Glioblastoma | IL-13-CD3ζ | Second |
| IL-13R-a2 | Medulloblastoma | IL-13-CD3ζ | Second |
| KDR | Tumor neovasculature | ScFv-FcεRIγ | First |
| k-light chain | B-cell malignancies | ScFv-CD3ζ | First |
| k-light chain | (B-NHL, CLL) | ScFv-CD28-CD3ζ vs CD3ζ | Second |
| LeY | Carcinomas | ScFv-FcεRIγ | First |
| LeY | Epithelial derived tumors | ScFv-CD28-CD3ζ | Second |
| L1 cell adhesion molecule | Neuroblastoma | ScFv-CD3ζ | First |
| MAGE-A1 | Melanoma | ScFV-CD4-FcεRIγ | Second |
| MAGE-A1 | Melanoma | ScFV-CD28-FcεRIγ | Second |
| Mesothelin | Various tumors | ScFv-CD28-CD3ζ | Second |
| Mesothelin | Various tumors | ScFv-41BB-CD3ζ | Second |
| Mesothelin | Various tumors | ScFv-CD28-41BB-CD3ζ | Third |
| Murine CMV infected cells | Murine CMV | Ly49H-CD3ζ | Second |
| MUC1 | Breast, Ovary | ScFV-CD28-OX40-CD3ζ | Third |
| NKG2D ligands | Various tumors | NKG2D-CD3ζ | First |
| Oncofetal antigen (h5T4) | Various tumors | ScFv-CD3ζ (vaccination) | First |
| PSCA | Prostate carcinoma | ScFv-b2c-CD3ζ | Second |
| PSMA | Prostate/tumor vasculature | ScFv-CD3ζ | First |
| PSMA | Prostate/tumor vasculature | ScFv-CD28-CD3ζ | Second |
| PSMA | Prostate/tumor vasculature | ScFv-CD3ζ | First |
| TAA targeted by mAh IgE | Various tumors | FceRI-CD28-CD3ζ (+a-TAA IgE mAb) | Third |
| TAG-72 | Adenocarcinomas | scFv-CD3ζ | First |
| VEGF-R2 | Tumor neovasculature | scFv-CD3ζ | First |

Chemotherapy Agents

In one aspect of the present invention, the modified immune cells or IFN are administered in combination with a chemotherapy agent. The chemotherapy agent may be any agent having a therapeutic effect on one or more types of cancer. Many chemotherapy agents are currently known in the art. Types of chemotherapy drugs include, by way of non-limiting example, alkylating agents, antimetabolites, anti-tumor antibiotics, topoisomerase inhibitors, mitotic inhibitors, corticosteroids, and the like.

Non-limiting examples of chemotherapy drugs include: nitrogen mustards, such as mechlorethamine (nitrogen mustard), chlorambucil, cyclophosphamide (Cytoxan®), ifosfamide, and melphalan); Nitrosoureas, such as streptozocin, carmustine (BCNU), and lomustine; alkyl sulfonates, such as busulfan; Triazines, such as dacarbazine (DTIC) and temozolomide (Temodar®); ethylenimines, such as thiotepa and altretamine (hexamethylmelamine); platinum drugs, such as cisplatin, carboplatin, and oxalaplatin; 5-fluorouracil (5-FU); 6-mercaptopurine (6-MP); Capecitabine (Xeloda®); Cytarabine (Ara-CR); Floxuridine; Fludarabine; Gemcitabine (Gemzar®); Hydroxyurea; Methotrexate; Pemetrexed (Alimta®); anthracyclines, such as Daunorubicin, Doxorubicin (Adriamycin®), Epirubicin, Idarubicin; Actinomycin-D; Bleomycin; Mitomycin-C; Mitoxantrone; Topotecan; Irinotecan (CPT-11); Etoposide (VP-16); Teniposide; Mitoxantrone; Taxanes: paclitaxel (Taxol®) and docetaxel (Taxotere®); Epothilones: ixabepilone (Ixempra®); Vinca alkaloids: vinblastine (Velban®), vincristine (Oncovin®), and vinorelbine (Navelbine®); Estramustine (Emcyt®); Prednisone; Methylprednisolone (Solumedrol®); Dexamethasone (Decadron®); L-asparaginase; bortezomib (Velcade®). Additional chemotherapy agents are listed, for example, in U.S. Patent Application Pub. No. 2008/0300165, which is incorporated herein by reference in its entirety.

Doses and administration protocols for chemotherapy drugs are well-known in the art. The skilled clinician can readily determine the proper dosing regimen to be used, based on factors including the chemotherapy agent(s) administered, type of cancer being treated, stage of the cancer, age and condition of the patient, patient size, location of the tumor, and the like.

Radiotherapy Agents

In one aspect of the present invention, the modified immune cells or IFN are administered in combination with a radiotherapeutic agent. The radiotherapeutic agent may be any such agent having a therapeutic effect on one or more types of cancer. Many radiotherapeutic agents are currently known in the art. Types of radiotherapeutic drugs include, by way of non-limiting example, X-rays, gamma rays, and charged particles. In one embodiment, the radiotherapeutic agent is delivered by a machine outside of the body (external-beam radiation therapy). In a preferred embodiment, the radiotherapeutic agent is placed in the body near the tumor/cancer cells (brachytherapy) or is a systemic radiation therapy.

External-beam radiation therapy may be administered by any means. Exemplary, non-limiting types of external-beam radiation therapy include linear accelerator-administered radiation therapy, 3-dimensional conformal radiation therapy (3D-CRT), intensity-modulated radiation therapy (IMRT), image-guided radiation therapy (IGRT), tomotherapy, stereotactic radiosurgery, photon therapy, stereotactic body radiation therapy, proton beam therapy, and electron beam therapy.

Internal radiation therapy (brachytherapy) may be by any technique or agent. Exemplary, non-limiting types of internal radiation therapy include any radioactive agents that can be placed proximal to or within the tumor, such as Radium-226 (Ra-226), Cobalt-60 (Co-60), Cesium-137 (Cs-137), cesium-131, Iridium-192 (Ir-192), Gold-198 (Au-198), Iodine-125 (1-125), palladium-103, yttrium-90, etc. Such agents may be administered by seeds, needles, or any other route of administration, and may be temporary or permanent.

Systemic radiation therapy may be by any technique or agent. Exemplary, non-limiting types of systemic radiation therapy include radioactive iodine, ibritumomab tiuxetan (Zevalin®), tositumomab and iodine I 131 tositumomab (Bexxar®), samarium-153-lexidronam (Quadramet®), strontium-89 chloride (Metastron®), metaiodobenzylguanidine, lutetium-177, yttrium-90, strontium-89, and the like.

In one embodiment, a radiosensitizing agent is also administered to the patient. Radiosensitizing agents increase the damaging effect of radiation on cancer cells.

Doses and administration protocols for radiotherapy agents are well-known in the art. The skilled clinician can readily determine the proper dosing regimen to be used, based on factors including the agent(s) administered, type of cancer being treated, stage of the cancer, location of the tumor, age and condition of the patient, patient size, and the like.

Anti-Cancer Vaccines

In one aspect of the present invention, the modified immune cells or IFN are administered in combination with an anti-cancer vaccine (also called cancer vaccine). Anti-cancer vaccines are vaccines that either treat existing cancer or prevent development of a cancer by stimulating an immune reaction to kill the cancer cells. In a preferred embodiment, the anti-cancer vaccine treats existing cancer.

The anti-cancer vaccine may be any such vaccine having a therapeutic effect on one or more types of cancer. Many anti-cancer vaccines are currently known in the art. Such vaccines include, without limitation, dasiprotimut-T, Sipuleucel-T, talimogene laherparepvec, HSPPC-96 complex (Vitespen), L-BLP25, gp100 melanoma vaccine, and any other vaccine that stimulates an immune response to cancer cells when administered to a patient.

Antibodies

In one aspect of the present invention, the modified immune cells or IFN are administered in combination with an anti-tumor antibody. That is, antibodies specific for a particular type of cancer (e.g., a cell surface protein expressed by the target cancer cells) can be administered to a patient having cancer. The antibodies may be monoclonal antibodies, polyclonal antibodies, chimeric antibodies, antibody fragments, human antibodies, humanized antibodies, or non-human antibodies (e.g. murine, goat, primate, etc.). The therapeutic antibody may be specific for any tumor-specific or tumor-associated antigen. See, e.g. Scott et al., *Cancer Immunity* 2012, 12:14, which is incorporated herein by reference in its entirety.

Non-limiting examples include trastuzumab (Herceptin®), bevacizumab (Avastin®), cetuximab (Erbitux®), panitumumab (Vectibix®), ipilimumab (Yervoy®), rituximab (Rituxan®), alemtuzumab (Campath®), ofatumumab (Arzerra®), gemtuzumab ozogamicin (Mylotarg®), brentuximab vedotin (Adcetris®), $^{90}$Y-ibritumomab tiuxetan (Zevalin®), and $^{131}$I-tositumomab (Bexxar®).

Additional antibodies are provided in Table 1.

TABLE 1

Anti-cancer antibodies

| Proprietary name | Trade name | Target; Format | Indication first approved or reviewed |
|---|---|---|---|
| Necitumumab | (Pending) | EGFR; Human IgG1 | Non-small cell lung cancer |
| Nivolumab | Opdivo | PD1; Human IgG4 | Melanoma |
| Dinutuximab | (Pending) | GD2; Chimeric IgG1 | Neuroblastoma |
| Blinatumomab | Blincyto | CD19, CD3; Murine bispecific tandem scFv | Acute lymphoblastic leukemia |
| Pembrolizumab | Keytruda | PD1; Humanized IgG4 | Melanoma |
| Ramucirumab | Cyramza | VEGFR2; Human IgG1 | Gastric cancer |
| Obinutuzumab | Gazyva | CD20; Humanized IgG1; Glycoengineered | Chronic lymphocytic leukemia |
| Ado-trastuzumab emtansine | Kadcyla | HER2; humanized IgG1; immunoconjugate | Breast cancer |
| Pertuzumab | Perjeta | HER2; humanized IgG1 | Breast Cancer |
| Brentuximab vedotin | Adcetris | CD30; Chimeric IgG1; immunoconjugate | Hodgkin lymphoma, systemic anaplastic large cell lymphoma |

TABLE 1-continued

Anti-cancer antibodies

| Proprietary name | Trade name | Target; Format | Indication first approved or reviewed |
| --- | --- | --- | --- |
| Ipilimumab | Yervoy | CTLA-4; Human IgG1 | Metastatic melanoma |
| Ofatumumab | Arzerra | CD20; Human IgG1 | Chronic lymphocytic leukemia |

Immune Checkpoint Inhibitors

In one aspect of the present invention, the modified immune cells or IFN are administered in combination with a checkpoint inhibitor. Immune checkpoint proteins are made by some types of immune system cells, such as T cells, and some cancer cells. These proteins, which can prevent T cells from killing cancer cells, are targeted by checkpoint inhibitors. Checkpoint inhibitors increase the T cells' ability to kill the cancer cells. Examples of checkpoint proteins found on T cells or cancer cells include PD-1/PD-L1 and CTLA-4/B7-1/B7-2.

In one embodiment, the checkpoint inhibitor is an antibody to a checkpoint protein, e.g., PD-1, PDL-1, or CTLA-4. Checkpoint inhibitor antibodies include, without limitation, BMS-936559, MPDL3280A, MedI-4736, Lambrolizumab, Alemtuzumab, Atezolizumab, Ipilimumab, Nivolumab, Ofatumumab, Pembrolizumab, and Rituximab.

Treatment Methods

In one aspect is provided a method for treating a patient having a plurality of HLA-negative cancer cells or cancer cells with reduced HLA expression with interferon-alpha ("IFN-alpha") in an amount sufficient to expand and/or activate immune cells such that the activated and/or expanded immune cells kill one or more of HLA-negative cancer cells or the cancer cells with reduced HLA expression.

In one embodiment, the method comprises identifying a patient having a cancer with reduced HLA expression. In one embodiment, the method comprises identifying a patient having a cancer which does not express HLA. In one embodiment, the method comprises determining HLA expression of a cancer in a patient before and/or after treatment of the patient with an anti-cancer agent, such as a T-cell therapy. In one embodiment, the method comprises identifying a patient having a cancer amenable to treatment with IFN-alpha as described herein by determining HLA expression of a cancer in a patient before and/or after treatment. In one embodiment, the method comprises selecting a patient having a cancer that does not express HLA or that has reduced HLA expression.

In one embodiment, the amount sufficient to expand and/or activate immune cells is a sub-therapeutic amount of the IFN-alpha. It is contemplated that administration of a sub-therapeutic amount of IFN-alpha can still activate, or expand the immune cells, including NK cells, such that the activated and/or expanded immune cells can kill one or more of HLA-negative cancer cells or cancer cells with reduced HLA expression. In one embodiment, the sub-therapeutic amount of IFN-alpha can be about 1%, about 5%, about 10%, about 15%, about 20%, about 25%, about 30%, about 35%, about 40%, about 45%, about 50%, about 55%, or about 60% of a therapeutic dosage of the IFN-alpha. In another embodiment, the IFN-alpha is administered in an amount ranging from about $5 \times 10^1$ U/m$^2$ to about $2 \times 10^5$ U/m$^2$. Administration of a sub-therapeutic amount of IFN-alpha allows for greater targeting of the immune cells (e.g., NK cells) to the tumor, or decreasing any potential side effects associated with IFN-alpha, or both. In one embodiment, to expand, activate, and/or stimulate the immune cells, the IFN-alpha can be administered orally, via vein injection, muscle injection, peritoneal injection, subcutaneous injection, nasal or mucosal administration, or by inhalation.

As discussed, cancers may develop one or more escape mechanisms to evade immunotherapy, including T-cell-mediated therapy, by reducing the expression of HLA on the cancer cell surface. It is contemplated that the methods described herein result in recognition and killing of the cancer cells with no or reduced HLA expression. In one aspect of the invention, the cancer comprise a population of cancer cells that initially express an HLA prior to comprising a population that is HLA-negative or have reduced HLA expression. In one embodiment, the patient has received or is selected based upon having received an immunotherapy for the cancer. In one embodiment, the immunotherapy is a T-cell therapy. In one embodiment, the immunotherapy targeted the HLA positive cells in the patient's cancer cell population, resulting in a reduction in HLA positive cells within the population.

In one embodiment, the IFN-alpha is administered as part of a combination therapy. In another embodiment, the combination therapy comprises one or more of chemotherapy, radiotherapy, and immunotherapy.

In addition to expanding and activating the endogenous immune cells, e.g., NK cells, IFN-alpha can also expand and activate the immune cells ex vivo before the expanded and activated immune cells are administered back to a patient with cancers comprising cells with no or reduced expression of HLA. One aspect of the invention relates to a method for treating a cancer, which comprises administering an immune cell to a subject in need thereof, wherein said immune cell is activated by IFN-alpha, further wherein the cancer has no or reduced expression of a HLA compared to a normal control. In one embodiment, the immune cell is a T-cell, a B-cell, or a NK-cell. In one embodiment, the immune cells, including the NK cells, are activated by incubating the immune cell with the IFN-alpha ex vivo. In another embodiment, the immune cell is incubated ex vivo with the IFN-alpha at a concentration from $5 \times 10^1$ U/$1 \times 10^6$ cells to $1 \times 10^4$ U/$1 \times 10^6$ cells.

In one embodiment, the HLA is a class I HLA antigen, a class II HLA antigen, or a class III HLA antigen. Preferably, the HLA is a class I HLA antigen and class II HLA antigen. In another embodiment, the source of the NK cells or the immune cells is autologous, allogeneic, or xenographic. In another embodiment, the NK cells or the immune cells are administered intravenously, intraperitoneally, intramuscularly, and subcutaneously.

In one embodiment, IFN-alpha can be one or more of IFN-alpha 1, IFN-alpha 2, IFN-alpha 4, IFN-alpha 5, IFN-alpha 6, IFN-alpha 7, IFN-alpha 8, IFN-alpha 10, IFN-alpha 14, IFN-alpha 16, IFN-alpha 17, or IFN-alpha 21. Preferably, IFN-alpha is IFN-alpha 2, IFN-alpha 8, or IFN-alpha 10. In other preferred embodiments, the IFN-alpha is IFN-alpha 8.

In one embodiment, the IFN is a synthetic or recombinant IFN-alpha.

In one embodiment, the immune cells, such as NK cells, are administered in combination with an anti-tumor agent. In another embodiment, the anti-tumor agent is a chemotherapy agent, a radiotherapy agent, an anti-cancer antibody, an immune checkpoint inhibitor, or an anti-cancer vaccine.

In one embodiment, the immune cell is modified to express a tumor cell homing receptor on the outer cell surface of the immune cell. In another embodiment, the tumor cell homing receptor is a chimeric antigen receptor, an Fc receptor, or combinations thereof. In one embodiment, the immune cell is a T-cell, a B-cell, or a NK cell. In another embodiment, the patient or subject is human.

Cancers or tumors that can be treated by the cells and methods described herein include, but are not limited to: biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors escaping immune recognition include glioma, colon carcinoma, colorectal cancer, lymphoid cell-derived leukemia, choriocarcinoma, and melanoma.

Dose and Administration

The IFN-alpha, as described herein, are administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result.

The anti-cancer agent may be administered by any appropriate method. Dosage, treatment protocol, and routes of administration for anti-cancer agents, including chemotherapeutic agents, radiotherapeutic agents, anti-cancer antibodies, immune checkpoint inhibitors, and anti-cancer vaccines, are known in the art and/or within the ability of a skilled clinician to determine, based on the type of treatment, type of cancer, etc.

The length of time and modes of administration of IFN-alpha will vary, depending on the immune cells, type of tumor being treated, condition of the patient, and the like. Determination of such parameters is within the capability of the skilled clinician.

A variety of administration routes are available. The methods of the invention, generally speaking, may be practiced using any mode of administration that is medically acceptable, meaning any mode that produces effective levels of the active compounds without causing clinically unacceptable adverse effects.

Modes of administration include oral, rectal, topical, nasal or mucosal, intradermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. In one embodiment, the IFN-alpha is administered orally, via vein injection, muscle injection, peritoneal injection, subcutaneous injection, nasal or mucosal administration, or by inhalation via an inspirator.

EXAMPLES

The following examples are for illustrative purposes only and should not be interpreted as limitations of the claimed invention. There are a variety of alternative techniques and procedures available to those of skill in the art which would similarly permit one to successfully perform the intended invention.

Example 1

NK cells are isolated from the mice using the EasySep™ Mouse NK Cell Isolation Kit (STEMCELL™ Technologies) following the manufacturer's protocol. Isolated NK cells are incubated with the culture medium containing IFN-alpha (Lee Biomolecular, San Diego, Calif.; $1 \times 10^3$ U/$1 \times 10^6$ cells) at 37° C. and 5% $CO_2$ for 7-30 days. The culture medium is changed every 3 days with fresh IFN-alpha. Every 5 days, expanded NK cells are transferred to T25 flask or T75 flasks at a concentration of $0.5 \times 10^6$ cells.

Nude mice are injected with HLA-negative tumor cells (subcutaneous injection) to form a tumor that expresses no or reduced levels of HLA.

One to three days after the formation of tumors in the mice, the mice are injected via intravenous injection with $5 \times 10^6$ NK cells that are treated with IFN-alpha. The mice injected with the untreated NK cells are used as control. Tumor growth in mice injected with treated NK cells is delayed compared to mice injected with untreated NK cells.

Example 2

Nude mice are injected with HLA-negative tumor cells (subcutaneous injection) to form a tumor that expresses no or reduced levels of HLA.

One to three days after the formation of tumor in the mice, the mice are injected subcutaneously with control vehicle and IFN-alpha every three days at $1 \times 10^4$ U/$m^2$ for total 21 days. Tumor growth in mice injected with IFN-alpha is delayed compared to mice injected with control vehicle. It contemplated that the dosage of $1 \times 10^4$ U/$m^2$ for IFN-alpha is below the minimal therapeutic amount that would lead IFN-alpha to have any direct effect on tumor growth.

What is claimed is:

1. A method for treating a cancer in a patient, said cancer having a plurality of HLA-negative cancer cells or cancer cells with reduced HLA expression, the method comprising administering to said patient interferon alpha (IFN-alpha) in a sub-therapeutic amount sufficient to expand and/or activate NK cells in the patient such that the activated and/or expanded NK cells kill one or more of said HLA-negative cancer cells or said cancer cells with reduced HLA expression; wherein the sub-therapeutic amount is about $1 \times 10^4$ $U/m^2$.

2. The method of claim 1, wherein the patient is HLA-negative or has a reduced expression of a class I HLA, a class II HLA, or a class III HLA.

3. The method of claim 1, wherein the IFN-alpha comprises one or more of IFN-alpha 1, IFN-alpha 2, IFN-alpha 4, IFN-alpha 5, IFN-alpha 6, IFN-alpha 7, IFN-alpha 8, IFN-alpha 10, IFN-alpha 14, IFN-alpha 16, IFN-alpha 17, or IFN-alpha 21.

4. The method of claim 1, wherein the patient is selected based upon having a reduced HLA expression.

5. The method of claim 1, wherein the patient is receiving or is selected based upon having received an immunotherapy for the cancer.

6. The method of claim 5, wherein the immunotherapy comprises a T-cell therapy.

7. The method of claim 1, wherein the IFN-alpha is administered in combination with an anti-tumor agent.

8. The method of claim 7, wherein the anti-tumor agent comprises one or more of chemotherapy, radiotherapy, an anti-cancer vaccine, an anti-cancer antibody, or an immune checkpoint inhibitor.

* * * * *